United States Patent
Pacofsky et al.

(10) Patent No.: US 8,034,954 B2
(45) Date of Patent: Oct. 11, 2011

(54) CALCIUM CHANNEL ANTAGONISTS

(75) Inventors: Gregory J. Pacofsky, Raleigh, NC (US);
Mark J. Suto, Chapel Hill, NC (US);
Paul Christopher Fritch, Cary, NC (US)

(73) Assignee: Icagen, Inc., Durham, NC (US)

( * ) Notice: Subject to any disclaimer, the term of this patent is extended or adjusted under 35 U.S.C. 154(b) by 328 days.

(21) Appl. No.: 11/613,872

(22) Filed: Dec. 20, 2006

(65) Prior Publication Data

US 2007/0173504 A1     Jul. 26, 2007

Related U.S. Application Data

(60) Provisional application No. 60/753,439, filed on Dec. 22, 2005.

(51) Int. Cl.
*C07D 417/12* (2006.01)
*C07D 417/14* (2006.01)
*A61K 31/427* (2006.01)
*A61K 31/4427* (2006.01)
*A61K 31/497* (2006.01)
*A61K 31/506* (2006.01)
*A61P 25/04* (2006.01)
*A61P 25/08* (2006.01)
*A61P 29/02* (2006.01)

(52) U.S. Cl. ........ 548/146; 548/182; 548/184; 544/328; 544/406; 546/269.7; 514/255.05; 514/256; 514/336; 514/365; 514/369

(58) Field of Classification Search ............... 548/146, 548/182, 184; 514/365, 369, 370, 242, 255.05, 514/256, 336; 544/182, 326, 327, 407, 328, 544/405; 546/269.7
See application file for complete search history.

(56) References Cited

U.S. PATENT DOCUMENTS

| | | | |
|---|---|---|---|
| 4,210,762 A | 7/1980 | Howe | |
| 6,335,327 B1 | 1/2002 | Ogawa et al. | |
| 6,355,635 B1 | 3/2002 | Elliott et al. | |
| 6,706,717 B2 * | 3/2004 | Barrish et al. | 514/254.02 |
| 2003/0199523 A1 | 10/2003 | Snutch | |
| 2004/0038990 A1 * | 2/2004 | Guba et al. | 514/255.05 |
| 2005/0038073 A1 | 2/2005 | Neidhart et al. | |
| 2005/0038089 A1 * | 2/2005 | Neidhart et al. | 514/370 |

FOREIGN PATENT DOCUMENTS

| | | |
|---|---|---|
| DE | 19858192 A1 | 6/2000 |
| EP | 1140921 B1 | 4/2003 |
| WO | WO 98/03505 A2 | 1/1998 |
| WO | WO 2005037825 A2 * | 4/2005 |
| WO | WO 2005/051932 A1 | 6/2005 |
| WO | WO 2006/093247 A1 | 9/2006 |

OTHER PUBLICATIONS

Triggle, D. J., Biochemical Pharmacology, 74, 1-9, 2007.*
Forlani et al., Gazzeta Chimica Italiana, 113(11-12), 807-810, 1983; CA 101: 130624,1984.*
Foye et al., Journal of the Pharmaceutical Association, Scientific Edition, 45, 461-463, 1956; CA 51: 5538, 1957.*
International search Report mailed on Aug. 18, 2008, for PCT Application No. PCT/US06/48722 filed on Dec. 20, 2006, 2 pages.
Lombardo, Louis J. et al., "Discovery of N-(2-Chloro-6-methylphenyl)-2-(6-(4-(2-hydroxyethyl)-piperazin-1-yl)-2-methylpyrimidin-4-ylamino)thiazole-5-carboxamide (BMS-354825), a Dual Src/Abl Kinase Inhibitor with Potent Antitumor Activity in Preclinical Assays," *J. Med. Chem.* 47:6658-6661 (2004).
Todorovic, Slobodan M., "Mechanical and thermal antinociception in rats following systemic administration of mibefradil, a T-type calcium channel blocker," *Brain Research* 951:336-340 (2002).
Database Chemcats [Online], Chemical Abstracts Service, Columbus, Ohio, US; Sep. 10, 2002, XP002606612; retrieved from STN; Database accession No. 0026273110; * order number: T6775837 *.
Relevant portion of Supplementary European Search Report, Appln. No. EP 06847881.7, dated Oct. 25, 2010.

* cited by examiner

*Primary Examiner* — Venkataraman Balasubramanian
(74) *Attorney, Agent, or Firm* — Morgan, Lewis & Bockius, LLP

(57) ABSTRACT

The present invention provides novel calcium channel antagonists, and methods of treating disease sates using the novel antagonists.

24 Claims, No Drawings

CALCIUM CHANNEL ANTAGONISTS

CROSS-REFERENCES TO RELATED APPLICATIONS

The present application claims priority to U.S. Ser. No. 60/753,439, filed Dec. 22, 2005 herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Calcium is an important signaling molecule for many normal physiological processes in the human body. These include electrical signaling in the nervous system, as well as controlling heart and smooth muscle contraction, and hormone release. The entry of calcium into cells is regulated by a diverse set of proteins called calcium channels.

A fundamental role of Ca2+ channels is to translate an electrical signal on the surface membrane into a chemical signal within the cytoplasm, which, in turn, activates many important intracellular processes including contraction, secretion, neurotransmission and regulation of enzymatic activities and gene expression. Tsien et al., (1988), Trends Neurosci., vol. 11, pp. 431-438. Continuing studies have revealed that there are multiple types of Ca2+ currents as defined by physiological and pharmacological criteria. See, e.g., Catterall, W. A., (2000) Annul Rev. Cell Dev. Biol., 16:521-55; Llinas et al, (1992) Trends Neurosci, 15; 351-55; Hess, P. (1990) Ann. Rev. Neurosci. 56:337; Bean, B. P. (1989) Ann. Rev. Physiol. 51:367-384; and Tsien et al. (1988) Trends Neurosci. 11:431-38. In addition to exhibiting distinct kinetic properties, different Ca2+ channel types can be localized on different regions of a cell and have complex morphology. The calcium in nerve cells plays an important role in delivering signals between nerve cells. Voltage activated calcium channels play important roles including neuroexcitation, neurotransmission and hormone secretion, and regulation of gene transcription through Ca-dependent transcription factors.

Voltage dependent calcium channels have been classified by their electrophysiological and pharmacological properties (McCleskey, E. W. et al. *Curr Topics Membr* (1991) 39:295-326, and Dunlap, K. et al. *Trends Neurosci* (1995) 18:89-98). Voltage-gated calcium channels can be divided into Low Voltage Activated calcium channels (LVA), that are activated at a lower voltage, and High Voltage Activated (HVA) calcium channels, that are activated at a higher voltage with respect to typical resting membrane potentials. HVA channels are currently known to comprise at least three groups of channels, known as L-, N- and P/Q-type channels. These channels have been distinguished from one another electrophysiologically as well as biochemically on the basis of their pharmacology and ligand binding properties. The L-, N-, P/Q-type channels activate at more positive potentials (high voltage activated) and display diverse kinetics and voltage-dependent properties. To date, only one class of low-threshold calcium channels is known, the T-type calcium channels. These channels are so called because they carry a transient current with a low voltage of activation and rapid inactivation. (Ertel and Ertel (1997) Trends Pharmacol. Sci. 18:37-42.). In general, T-type calcium channels are involved in the generation of low threshold spikes to produce burst firing (Huguenard, J. R., Annul Rev. Physiol., 329-348, 1996).

Three genes are known to encode pore forming subunits of T-type calcium channels; CACNA1G (alpha1G, Cav3.1), CACNA1H (alpha1H, Cav3.2), and CACNA1I (alpha1I, Cav3.3) (see Perez-Reyes, Physiol Rev. 2003 83:117-61).

T-type calcium channels are located in the nervous system, cardiac & vascular smooth muscle; as well as a variety of endocrine cell types (see Perez-Reyes, Physiol Rev. 2003 83:117-61). Generally, T-type channels are believed to be involved in electrical pacemaker activity, low-threshold calcium spikes, neuronal oscillations and resonance (Perez-Reyes, *Physiol Rev.* 2003 83:117-61). The functional roles for T-type calcium channels in neurons include, membrane depolarization, calcium entry and burst firing. (White et al. (1989) Proc. Natl. Acad. Sci. USA 86:6802-6806). Functionally unique calcium channels allow for temporal and spatial control of intracellular calcium and support regulation of cellular activity.

T-type calcium channels have more negative activation ranges and inactivate more rapidly than other calcium channels. When the range of membrane potentials for activation and inactivation overlap, T-type calcium channels can undergo rapid cycling between open, inactivated, and closed states, giving rise to continuous calcium influx in a range of negative membrane potentials where HVA channels are not normally activated. The membrane depolarizing influence of T-type calcium channel activation can become regenerative and produce calcium action potentials and oscillations.

In addition to the variety of normal physiological functions mediated by calcium channels, they are also implicated in a number of human disorders. For example, changes to calcium influx into neuronal cells may be implicated in conditions such as epilepsy, stroke, brain trauma, Alzheimer's disease, multiinfarct dementia, other classes of dementia, Korsakoff's disease, neuropathy caused by a viral infection of the brain or spinal cord (e.g., human immunodeficiency viruses, etc.), amyotrophic lateral sclerosis, convulsions, seizures, Huntington's disease, amnesia, pain transmission, cardiac pacemaker activity or damage to the nervous system resulting from reduced oxygen supply, poison or other toxic substances (Goldin et al., U.S. Pat. No. 5,312,928). Other pathological conditions associated with elevated intracellular free calcium levels include muscular dystrophy and hypertension (Steinhardt et al., U.S. Pat. No. 5,559,004).

Low threshold spikes and rebound burst firing characteristic of T-type calcium currents is prominent in neurons from inferior olive, thalamus, hippocampus, lateral habenular cells, dorsal horn neurons, sensory neurons (DRG, nodose), cholinergic forebrain neurons, hippocampal intraneurons, CA1, CA3 dentate gyros pyramidal cells, basal forebrain neurons, amygdala neurons (Talley et al., J. Neurosci., 19: 1895-1911, 1999) and neurons in the thalamus (Suzaki and Rogawski, Proc. Natl. Acad. Sci. USA 86:7228-7232, 1998). As well, T-type channels are prominent in the some and dendrites of neurons that reveal robust Ca dependent burst firing behaviors such as the thalamic relay neurons and cerebellar Purkinje cells (Huguenard, J. R., Annul Rev. Physiol., 329-348, 1996). Consequently, improper functioning of these T-type calcium channels has been implicated in arrhythmias, chronic peripheral pain, inappropriate pain transmission in the central nervous system.

The reduction of in vivo hyperalgesic responses to thermal or mechanical stimuli induced by chemical agents (i.e. reducing agents, capsaicin) or experimental nerve injury (i.e. chronic constriction injury; spinal nerve ligation) by known T-type calcium channel antagonists mibefradil and/or ethosuximide suggests a role of the T-type calcium channels in peripheral nerve pain signaling (Todorovic, Neuron, 2001, 31:75-85; Todorovic and Lingle, J. Neurophysiol. 79:240-252, 1998, Flatters S J, Bennett G J. Pain. 2004 109:150-61; Dogrul et al; Pain. 2003 105:159-68; Matthews and Dickenson. Eur J Pharmacol. 2001 415:141-9). Furthermore, intrathecal administration of antisense oligonucleotides to alphalH (Cav3.2) T-type calcium channels in rodents has recently been shown to selectively inhibit the functional expression of T-type calcium currents in sensory neurons and reverse hyperalgesic, and allodynic, responses induced by experimental nerve injury (Bourinet et al EMBO J. 2005 24:315-24). Gene knockout of alpha1G (Cav3.1) T-type channels in mouse CNS is reported to increase the perception of visceral pain (Kim et al. Science. 2003 302:117-9).

T-type calcium channels promote oscillatory behavior, which has important consequences for epilepsy. The ability of a cell to fire low threshold spikes is critical in the genesis of oscillatory behavior and increased burst firing (groups of action potentials separated by about 50-100 ms). T-type calcium channels are believed to play a vital role in absence epilepsy, a type of generalized non-convulsive seizure. The evidence that voltage-gated calcium currents contribute to the epileptogenic discharge, including seizure maintenance and propagation includes: 1) a specific enhancement of T-type currents in the reticular thalamic (nRT) neurons which are hypothesized to be involved in the genesis of epileptic seizures in a rat genetic model for absence epilepsy (Tsakiridou et al., J. Neurosci., 15: 3110-3117, 1995); 2) antiepileptics against absence petit mal epilepsy (ethosuximide and dimethadione) have been shown at physiologically relevant doses to partially depress T-type currents in thalamic neurons (Courter et al., Ann. Neurol., 25:582-93, 1989; U.S. Pat. No. 6,358,706 and references cited therein), and; 3) T-type calcium channels underlie the intrinsic bursting properties of particular neurons that are hypothesized to be involved in epilepsy (nRT, thalarnic relay and hippocampal pyramidal cells) (Huguenard).

The T-type calcium channels have been implicated in thalamic oscillations and cortical synchrony, and their involvement has been directly implicated in the generation of cortical spike waves that are thought to underlie absence epilepsy and the onset of sleep (McCormick and Bal, Annul Rev. Neurosci., 20: 185-215, 1997). Oscillations of neural networks are critical in normal brain function such during sleep-wave cycles. It is widely recognized that the thalamus is intimately involved in cortical rhythmogenesis. Thalamic neurons most frequently exhibit tonic firing (regularly spaced spontaneous firing) in awake animals, whereas phasic burst firing is typical of slow-wave sleep and may account for the accompanying spindling in the cortical EEG. The shift to burst firing occurs as a result of activation of a low threshold Ca2+ spike which is stimulated by synaptically mediated inhibition (i.e., activated upon hyperpolarization of the RP). The reciprocal connections between pyramidal neurons in deeper layers of the neocortex, cortical relay neurons in the thalamus, and their respective inhibitory interneurons are believed to form the elementary pacemaking circuit.

Tremor can be controlled through the basal ganglia and the thalamus, regions in which T-type calcium channels are strongly expressed (Talley et al J Neurosci. 1999 19:1895-911). T-type calcium channels have been implicated in the pathophysiology of tremor since the anti-epileptic drug ethosuximide is used for treating tremor, in particular, tremor associated with Parkinson's disease, essential tremor, or cerebellar disease (U.S. Pat. No. 4,981,867; D. A. Prince).

It is well documented that cortisol is the precursor for glucocorticoids and prolonged exposure to glucocorticoids causes breakdown of peripheral tissue protein, increased glucose production by the liver and mobilization of lipid from the fat depots. Furthermore, individuals suffering from anxiety and stress produce abnormally high levels of glucocorticoids. Consequently, drugs that would regulate these levels would aid in the treatment of stress disorders. In this regard, the observations (Enyeart et al., Mol. Endocrinol., 7:1031-1040, 1993) that T-type channels in adrenal zone fasciculata cells of the adrenal cortex modulate cortisol secretion will greatly aid in the identification of such a therapeutic candidate.

T-type calcium channels may also be involved sperm production. Sertoli cells secrete a number of proteins including transport proteins, hormones and growth factors, enzymes which regulate germinal cell development and other biological processes related to reproduction (Griswold, Int. Rev. Cytol., 133-156, 1988). While the role of T-type calcium channels remains to be fully elucidated, it is believed that they may be important in the release of nutrients, inhibin B, and/or plasminogen activator and thus may impact sperm production. According to researchers, the inhibition of T-type calcium channels in sperm during gamete interaction inhibits zona pellucida-dependent Ca2+ elevations and inhibits acrosome reactions, thus directly linking sperm T-type calcium channels to fertilization.

In view of the above, pharmacological modulation of T-type calcium channel function is very important and therapeutic moieties capable of modulating T-type currents may find utility in the practice of medicine, i.e., calcium channel blockers for the treatment of pain, epilepsy, hypertension, and angina pectoris etc. Compounds identified thereby may be candidates for use in the treatment of disorders and conditions associated with T-channel activity in humans and animals. Such activities include, but are not limited to, those involving a role in muscle excitability, secretion and pacemaker activity, Ca2+ dependent burst firing, neuronal oscillations, and potentiation of synaptic signals, for improving arterial compliance in systolic hypertension, or improving vascular tone, such as by decreasing vascular welling, in peripheral circulatory disease, and others. Other disorders include, but are not limited to hypertension; cardiovascular disorders (e.g. myocardial infarct, cardiac arrhythmia, heart failure and angina pectoris); neurological disorders (e.g. epilepsy, pain, schizophrenia, depression and sleep); peripheral muscle disorders; respiratory disorders; and endocrine disorders. The present invention meets these and other needs in the art.

BRIEF SUMMARY OF THE INVENTION

It has been discovered that substituted 5-membered nitrogen-containing heteroaryls may be used to antagonize calcium channels.

In one aspect, the calcium channel antagonist of the present invention has the formula:

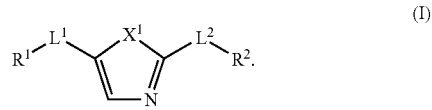

In the compound of Formula (I), $X^1$ is —S—, —O—, or —N($R^3$)—. $R^1$ is substituted or unsubstituted cycloalkyl, substituted or unsubstituted heterocycloalkyl, substituted or unsubstituted aryl, or substituted or unsubstituted heteroaryl.

$R^2$ is substituted or unsubstituted heteroaryl, substituted or unsubstituted heterocycloalkyl, substituted or unsubstituted cycloalkyl, or substituted or unsubstituted aryl. $L^1$ and $L^2$ are independently a bond, substituted or unsubstituted alkylene, substituted or unsubstituted heteroalkylene, —S(O)$_n$—, —N($R^4$)—, —N($R^4$)C(O)—, —N($R^4$)C(O)O—, —N($R^4$)C(O)N($R^4$)—, —C(O)—, —O—, —C(O)N($R^4$)—, —CH(O$R^4$)—, —CH$_2$—, —CH$_2$O—. The symbol n represents an integer from 0 to 2. $R^3$ and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, the present invention provides pharmaceutical compositions comprising a pharmaceutically acceptable carrier and an antagonist of the present invention (e.g. a compound of the present invention or a complex of the present invention).

In yet another aspect, the present invention provides a method for decreasing ion flow through a voltage-dependant calcium channel in a cell. The method includes contacting the cell with a calcium channel-closing amount of an antagonist of the present invention.

In still another aspect, the present invention provides a method for treating a disease through antagonizing calcium ion flow through calcium channels.

DETAILED DESCRIPTION OF THE INVENTION

I. Abbreviations and Definitions

The abbreviations used herein have their conventional meaning within the chemical and biological arts.

Where moieties are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight or branched chain, or combination thereof, which may be fully saturated, mono- or polyunsaturated and can include di- and multivalent radicals, having the number of carbon atoms designated (i.e. $C_1$-$C_{10}$ or 1- to 10-membered means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. An "alkenylene," is an alkylene that includes at least one carbon-carbon double bond, and an "alkynylene" is an alkylene that includes at least one carbon-carbon triple bond. A homoalkylene is an alkylene that does not include carbon-carbon double bonds or triple bonds.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—C(=O)—CH$_3$, —CH$_2$—CH$_2$—CH$_2$—C(=O)—O—C(CH$_3$)—CH$_3$, —CH$_2$—CH$_2$—CH$_2$—C(=O)—N—CH(CH$_3$), —CH$_2$—CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated and unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom. "Oxa," as used herein, means an oxygen that is bonded to two carbon atoms. "Thia," as used herein, means a sulfur that is bonded to two carbon atoms.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1 to 3 halogens, substituted or unsubstituted alkyl, alkoxy or thioalkoxy groups, or arylalkyl groups. When an antagonist of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, alkyl, heteroalkyl, aryl and heteroaryl. When an antagonist of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —C(O)—, —NR'—, —S—, —S(O)—, —S(O)$_2$—, or —S(O)$_2$NR'. The substituents R, R', R" and R'" are preferably independently selected from hydrogen or substituted or unsubstituted (C$_1$-C$_6$)alkyl.

As used herein, the term "heteroatom" is meant to include oxygen (O), nitrogen (N), and sulfur (S).

A "substituent group," as used herein, means a group selected from the following moieties:

(A) —OH, —NH$_2$, —SH, —CN, —CF$_3$, oxy, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2- to 20-membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active antagonists which are prepared with relatively nontoxic acids or bases, depending on the particular substituents found on the antagonists described herein. When antagonists of the present invention contain relatively acidic functionalities, base addition salts can be obtained by contacting the neutral form of such antagonists with a sufficient amount of the desired base, either neat or in a suitable inert solvent. Examples of pharmaceutically acceptable base addition salts include sodium, potassium, calcium, ammonium, organic amino, or magnesium salt, or a similar salt. When antagonists of the present invention contain relatively basic functionalities, acid addition salts can be obtained by contacting the neutral form of such antagonists with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science* 66: 1-19 (1977)). Certain specific antagonists of the present invention contain both basic and acidic functionalities that allow the antagonists to be converted into either base or acid addition salts.

The neutral forms of the antagonists are preferably regenerated by contacting the salt with a base or acid and isolating the parent antagonist in the conventional manner. The parent form of the antagonist differs from the various salt forms in certain physical properties, such as solubility in polar solvents.

In addition to salt forms, the present invention provides antagonists, which are in a prodrug form. Prodrugs of the antagonists described herein are those compounds or complexes that readily undergo chemical changes under physiological conditions, in vivo, to provide the antagonists of the present invention. Additionally, prodrugs can be converted to the antagonists of the present invention by chemical or biochemical methods in an ex vivo environment. For example, prodrugs can be slowly converted to the antagonists of the present invention when placed in a transdermal patch reservoir with a suitable enzyme or chemical reagent.

The term "ring" as used herein means a substituted or unsubstituted cycloalkyl, substituted or unsubstituted heterocycloalkyl, substituted or unsubstituted aryl, or substituted or unsubstituted heteroaryl. A ring includes fused ring moities. The number of atoms in a ring are typically defined by the number of members in the ring. For example, a "5- to 7-membered ring" means there are 5-7 atoms in the encircling arrangement. The ring optionally includes a heteroatom. Thus, the term "5- to 7-membered ring" includes, for example pyridinyl, piperidinyl and thiazolyl rings.

The term "poly" as used herein means at least 2. For example, a polyvalent metal ion is a metal ion having a valency of at least 2.

"Moiety" refers to the radical of a molecule that is attached to another moiety.

The symbol $\sim\!\!\sim\!\!\sim$, whether utilized as a bond or displayed perpendicular to a bond indicates the point at which the displayed moiety is attached to the remainder of the molecule.

Certain antagonists of the present invention can exist in unsolvated forms as well as solvated forms, including hydrated forms. In general, the solvated forms are equivalent to unsolvated forms and are encompassed within the scope of the present invention. Certain antagonists of the present invention may exist in multiple crystalline or amorphous forms. In general, all physical forms are equivalent for the uses contemplated by the present invention and are intended to be within the scope of the present invention.

Certain antagonists of the present invention possess asymmetric carbon atoms (optical centers) or double bonds; the racemates, diastereomers, geometric isomers and individual isomers are encompassed within the scope of the present invention.

The antagonists of the present invention may also contain unnatural proportions of atomic isotopes at one or more of the atoms that constitute such antagonists. For example, the antagonists may be radiolabeled with radioactive isotopes, such as for example tritium ($^3$H), iodine-125 ($^{125}$I) or carbon-14 ($^{14}$C). All isotopic variations of the antagonists of the present invention, whether radioactive or not, are encompassed within the scope of the present invention.

The following abbreviations may be used in the examples and throughout the specification:

g (grams); mg (milligrams);
L (liters); mL (milliliters);
µL (microliters); psi (pounds per square inch);
M (molar); mM (millimolar);
NaI (sodium iodide); Hz (Hertz);
MHz (megahertz); mol (moles);
mmol (millimoles); RT (ambient temperature);
min (minutes); h (hours);
mp (melting point); TLC (thin layer chromatography);
NaOH (sodium hydroxide); RP (reverse phase);
MeOH (methanol); i-PrOH (isopropanol);
Et$_3$N (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); CH$_2$Cl$_2$ (dichloromethane);
POCl$_3$ (phosphorous oxychloride); DMF (N,N-dimethylformamide);
CHCl$_3$ (chloroform); NaCl (sodium chloride);
Sodium sulfate (Na$_2$SO$_4$); DIEA (N,N-diisopropylethylamine);
HOAc (acetic acid); Et$_2$O (diethyl ether);
BOC (tert-butyloxycarbonyl); Ar (argon);

NH$_4$OH (Ammonium hydroxide); CBZ (benzyloxycarbonyl);

Ac (acetyl); atm (atmosphere);

EtOH (ethanol); NaH (sodium hydride);

HCl (hydrogen chloride); Me (methyl);

OMe (methoxy); Et (ethyl);

Et (ethyl); tBu (tert-butyl);

LC (liquid chromatography); ° C. (degrees Centigrade)

HI (hydrogen iodide); Pd-C (palladium on charcoal)

LCMS (liquid chromatography couple mass spectrometry)

Unless otherwise noted, the symbols and conventions used herein (processes, schemes and examples) are consistent with those used in the contemporary scientific literature, for example, the *Journal of the American Chemical Society* or the *Journal of Biological Chemistry*.

II. Calcium Channel Antagonists

In one aspect, the calcium channel antagonist of the present invention has the formula:

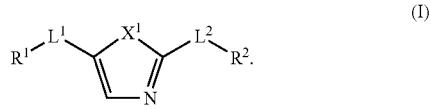

(I)

In the compound of Formula (I), $X^1$ is —S—, —O—, or —N(R$^3$)—. $R^1$ is substituted or unsubstituted cycloalkyl, substituted or unsubstituted heterocycloalkyl, substituted or unsubstituted aryl, or substituted or unsubstituted heteroaryl. $R^2$ is substituted or unsubstituted heteroaryl, substituted or unsubstituted heterocycloalkyl, substituted or unsubstituted cycloalkyl, or substituted or unsubstituted aryl. $L^1$ and $L^2$ are independently a bond, substituted or unsubstituted alkylene, substituted or unsubstituted heteroalkylene, —S(O)$_n$—, —N(R$^4$)—, —N(R$^4$)C(O)—, —N(R$^4$)C(O)O—, —N(R$^4$)C(O)N(R$^4$)—, —C(O)—, —O—, —C(O)N(R$^4$)—, —CH(OR$^4$)—, —CH$_2$—, —CH$_2$O—. The symbol n represents an integer from 0 to 2. $R^3$ and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^1$ is substituted or unsubstituted aryl (e.g. substituted or unsubstituted phenyl). $R^2$ may be substituted or unsubstituted aryl (e.g. substituted or unsubstituted phenyl) or substituted or unsubstituted heteroaryl (e.g. substituted or unsubstituted pyridinyl, or substituted or unsubstituted pyrimidinyl).

In some embodiments, $X^1$ is —S—; $R^1$ is substituted or unsubstituted aryl, or substituted or unsubstituted heteroaryl; $L^1$ is substituted or unsubstituted alkylene, —S(O)$_2$—, —N(R$^4$)—, or —O—; and $L^2$ is —S(O)$_2$—, —N(R$^4$)—, —O—, or —C(O)N(R$^4$)—. In other embodiments, $X^1$ is —S—; $R^1$ is substituted aryl, or substituted or unsubstituted heteroaryl; $R^2$ is substituted aryl, or substituted or unsubstituted heteroaryl; $L^1$ is —S(O)$_2$—; $L^2$ is —N(R$^4$)—; and $R^4$ is hydrogen, substituted or unsubstituted alkyl, or substituted or unsubstituted aryl.

$R^2$ may also have the formula

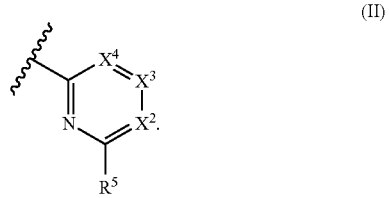

(II)

In Formula (II), $X^2$, $X^3$, and $X^4$ are independently =N—, or =C(R$^6$)—, wherein $X^3$ is =C(R$^6$)— when $X^2$ and/or $X^4$ is =N. $R^5$ and $R^6$ are independently hydrogen, halogen, —CF$_3$, -L$^3$-R$^7$, -L$^3$-OR$^7$, -L$^3$-NR$^8$R$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^3$ is a bond, substituted or unsubstituted alkylene (e.g. substituted or unsubstituted homoalkylene, substituted or unsubstituted alkenylene, substituted or unsubstituted alkynylene). $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ and an $R^9$ are optionally joined with the nitrogen to which they are attached to form a substituted or unsubstituted heterocycloalkyl, or substituted or unsubstituted heteroaryl. Two $R^7$ substituents are optionally joined with the oxygen to which they are attached to form a substituted or unsubstituted heterocycloalkyl (e.g. furanyl). $R^8$ and an $R^7$ are optionally joined with the nitrogen and oxygen to which they are attached, respectively, to form a substituted or unsubstituted heterocycloalkyl, or substituted or unsubstituted heteroaryl.

In some embodiments of Formula (II), $L^3$ is a bond, or unsubstituted alkylene. $L^3$ may also be a bond, or unsubstituted C$_1$-C$_8$ alkylene (e.g. a C$_1$-C$_8$ alkylene comprising an alkynylene linking moiety). $R^6$ may be -L$^3$-NR$^8$R$^9$. In some related embodiments, $L^3$ is a bond, $R^9$ is hydrogen; and $R^8$ is substituted or unsubstituted alkyl, or substituted or unsubstituted heteroalkyl.

In some embodiments of the compounds of Formula (I) and/or (II), $X^1$ is —S—; $R^1$ is substituted or unsubstituted aryl, or unsubstituted heteroaryl; $L^1$ is —S(O)$_2$—; $L^2$ is —N(R$^4$)—; and $R^5$ is hydrogen, halogen, substituted or unsubstituted alkyl, or substituted or unsubstituted aryl. $R^4$ may be hydrogen, unsubstituted alkyl, or unsubstituted heterocycloalkyl.

In some embodiments, the calcium channel antagonist has the formula:

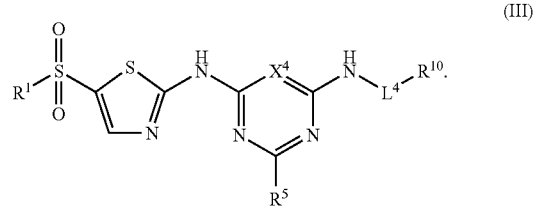

(III)

In Formula (III), $X^4$ is as defined above. $L^4$ is a bond or substituted or unsubstituted alkylene. $R^{10}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $L^4$ is unsubstituted alkylene. $R^1$ may be substituted or unsubstituted phenyl. $X^4$ may be =C($R^6$)—. In some related embodiments, $R^6$ is hydrogen.

In some embodiments, each substituted group described above in the compound of Formulae (I), (II) and/or (III) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, and/or substituted heteroalkylene, described above in the compounds of Formulae (I), (II) and/or (III) is substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I), (II) and/or (III), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, and/or each substituted or unsubstituted heteroalkylene is a substituted or unsubstituted 2 to 20 membered heteroalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

In another embodiment, the compounds of the present invention include the compounds of Tables 1-10, Examples 1-36, and/or Table A below.

TABLE A

| | |
|---|---|
| 2-(3,4-Dimethoxy-phenyl)-N-[5-(3-ethoxy-benzenesulfonyl)-thiazol-2-yl]-acetamide | 2-(3,4-Dimethoxy-phenyl)-N-[5-(4-fluoro-benzenesulfonyl)-thiazol-2-yl]-acetamide |
| 2-(3,4-Dimethoxy-phenyl)-N-[5-(3-trifluoromethoxy-benzenesulfonyl)-thiazol-2-yl]-acetamide | N-(5-Cyclopentylsulfanyl-thiazol-2-yl)-2-(3,4-dimethoxy-phenyl)-acetamide |
| 2-Benzo[1,3]dioxol-5-yl-N-[5-(3-fluoro-benzenesulfonyl)-thiazol-2-yl]-acetamide | [6-(3-Amino-3-methyl-butyl)-2-methyl-pyrimidin-4-yl]-[5-(3-ethoxy-benzenesulfonyl)-thiazol-2-yl]-amine |
| 2-(4-Chloro-phenyl)-N-[5-(3-methoxy-benzoyl)-thiazol-2-yl]-propionamide | 2-(3,4-Dimethoxy-phenyl)-N-[5-(3-ethoxy-benzenesulfonyl)-thiazol-2-yl]-N-methyl-acetamide |
| (1-Benzyl-piperidin-4-yl)-[5-(4-fluoro-benzenesulfonyl)-thiazol-2-yl]-amine | 1-[5-(4-Fluoro-benzenesulfonyl)-thiazol-2-yl]-3-(4-methoxy-benzyl)-urea |
| 5-(4-Fluoro-phenylsulfonyl)-thiazole-2-carboxylic acid 4-methoxy-benzylamide | 2-(4-Trifluoromethoxy-phenylsulfanyl)-thiazole-5-carboxylic acid 4-methoxy-benzylamide |
| [2-(3-Trifluoromethoxy-phenoxy)-thiazol-5-ylmethyl]-(4-trifluoromethyl-benzyl)-amine | 3-Phenyl-1-[2-(4-trifluoromethoxy-benzenesulfonyl)-thiazol-5-yl]-propan-1-ol |
| [2-(3,4-Dimethoxy-phenyl)-ethyl]-[5-(3-ethoxy-phenyl)-thiazol-2-ylmethyl]-carbamic acid tert-butyl ester | 3-(3,4-Dimethoxy-phenyl)-1-[5-(3-ethoxy-benzenesulfonyl)-thiazol-2-yl]-propan-1-one |
| 4-{4-[5-(3-Ethoxy-benzenesulfonyl)-thiazol-2-yl]-pyrimidin-2-yl}-morpholine | N-(2-Amino-2-methyl-propyl)-N'-[5-(3-ethoxy-benzenesulfonyl)-thiazol-2-yl]-2-methyl-pyrimidine-4,6-diamine |
| [5-(3-Ethoxy-benzenesulfonyl)-thiazol-2-yl]-[5-fluoro-2-methyl-6-(2-pyrrolidin-yl-ethoxy)-pyrimidin-4-yl]-amine | (3-{6-[5-(3-Ethoxy-benzenesulfonyl)-thiazol-2-ylamino]-2-methyl-pyrimidin-4-yl}-1,1-dimethyl-prop-2-ynyl)-carbamic acid tert-butyl ester |
| [5-(3-Ethoxy-benzenesulfonyl)-thiazol-2-yl]-[6-(3-methoxy-prop-1-ynyl)-2-methyl-pyrimidin-4-yl]-amine | N*2*-[5-(3-Ethoxy-benzenesulfonyl)-thiazol-2-yl]-N*5*-(2-pyrrolidin-1-yl-ethyl)-pyridine-2,5-diamine |
| [5-(3-Ethoxy-benzenesulfonyl)-thiazol-2-yl]-[2-methyl-6-((R)-pyrrolidin-3-yloxy)-pyrimidin-4-yl]-amine | N-[5-(3-Ethoxy-benzenesulfonyl)-thiazol-2-yl]-2-methyl-N'-(R)-pyrrolidin-3-yl-pyrimidine-4,6-diamine |
| N-[5-(3-Ethoxy-benzenesulfonyl)-thiazol-2-yl]-N'-(R)-pyrrolidin-3-yl-2-trifluoromethyl-pyrimidine-4,6-diamine | N*2*-[5-(4-Fluoro-benzenesulfonyl)-thiazol-2-yl]-N*5*-(2-methoxy-ethyl)-pyridine-2,5-diamine |
| [5-(3-Ethoxy-benzenesulfonyl)-thiazol-2-yl]-(6-methoxy-2-morpholin-4-yl-pyrimidin-4-yl)-amine | [5-(3-Ethoxy-benzenesulfonyl)-thiazol-2-yl]-(6-(2-methoxy-ethyl)-2-morpholin-4-yl-pyrimidin-4-yl)-amine |
| N*5*[5-(3-Fluoroy-benzenesulfonyl)-thiazol-2-yl]-N*2*-(2-pyrrolidin-1-yl-ethyl)-pyridine-2,5-diamine | |

III. Exemplary Syntheses

The following exemplary schemes illustrate methods of preparing the calcium channel antagonists of the present invention. These methods are not limited to producing the compounds shown, but can be used to prepare a variety of antagonists such as the compounds and complexes described above. The antagonists of the invention can also be produced by methods not explicitly illustrated in the schemes but are well within the skill of one in the art. The antagonists can be prepared using readily available starting materials or known intermediates. It is understood that protecting groups for sensitive or reactive functional groups may be employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes, including specific reaction conditions, and their order of execution is within the capabilities of those skilled in the art. Moreover, those skilled in the art will recognize that, where present, the compounds of the present invention include any appropriate stereoisomeric configuration, including racemic compounds and enantiomers. Where a single enantiomer is desired, it may be obtained by stereospecific synthesis or by resolution of the final product or any convenient intermediate.

Compounds of Formula I [$X^1$=S, $L^1$=S(O)$_n$, $L^2$=N($R^4$)C(O)] can be prepared according to the sequence shown in Scheme 1. Treatment of a 2-amino-5-halothiazole (2) with an appropriate meracaptan (1) provides the adduct 3. The reaction may optionally be heated, in an aprotic solvent such as THF, to temperatures between 25° C. and 150° C., typically 55° C. Oxidation of the sulfide, for example with Oxone®, provides the corresponding sulfonyl subunit 4. Acylation of the amino group may be accomplished via reaction with an acyl halide or another activated carbonyl compound, such as a mixed anhydride, generated in situ if necessary, and an added base in an appropriate solvent, such as $CH_2Cl_2$, to provide 5. Alternatively, amine 4 may react with agents such as isocyanates or chloroformates to deliver 5.

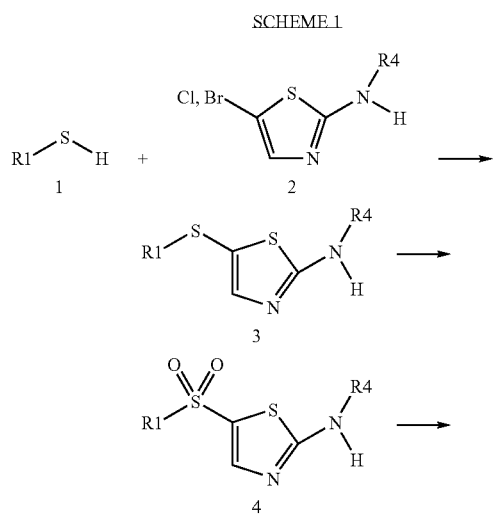

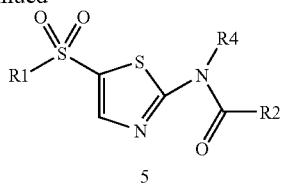

Compounds of Formula I [$X^1$=S, $L^1$=S(O)$_n$, $L^2$=N($R^4$)C(O)] may also be prepared according to the sequence shown in Scheme 2 and further detailed in the examples section following. Acylation of the amino group of a 2-amino-5-halothiazole (2) may be accomplished via reaction with an acyl halide or another activated carbonyl compound, such as a mixed anhydride, generated in situ if necessary, and an added base in an appropriate solvent, such as $CH_2Cl_2$, to provide 6. Subsequent reaction of 6 with an appropriate meracaptan (1) provide the adduct 7. The reaction may optionally be heated, in an aprotic solvent such as DMF, to temperatures between 50° C. and 150° C., typically 100° C. Oxidation of the sulfide, for example with Oxone®, provides the corresponding sulfonyl subunit and compounds of general structure 5.

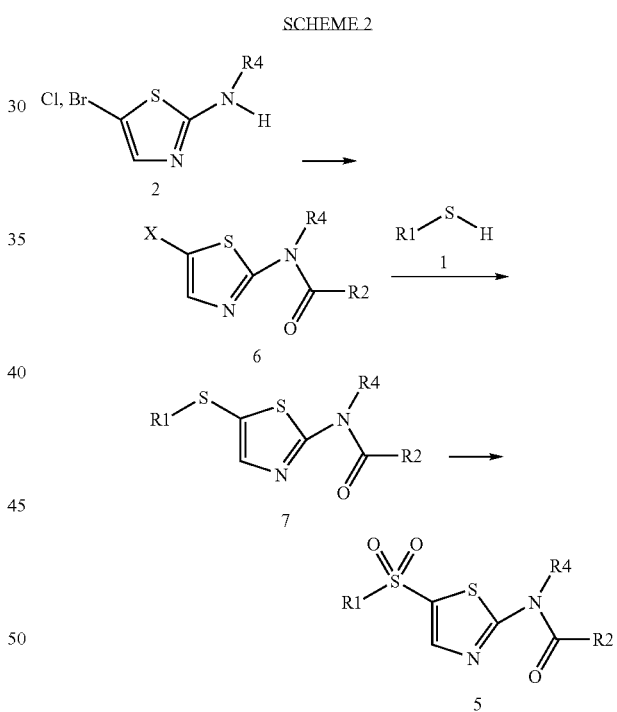

The pyrimidines ($X^2$=N, $X^3$=CR$^6$, $X^4$=CR$^6$) requisite for synthesis of compounds of Formula I may be prepared via procedures known in the literature (Inoue, S. et al, *J. Org. Chem.*, 1961, 26, 4504; Gomtsyan, A. et al *J. Med. Chem.* 2002, 45, 3639). As shown in Scheme 3, cyclization of a dialkyl, typically diethyl, malonate (9) with an appropriate amidine (10), usually at reflux in a matched alcoholic solvent, provides the dihydroxy-pyrimidines (11). Chlorination, typically using phosphorous oxychloride, provides the dichloro analogs (12) that may be reacted with ammonia (using either ammonium hydroxide or a solution of ammonia in an appropriate alcoholic solvent) or amines to obtain chloropyrimidines (8). Alternatively, conversion of the dichloropyrimidine to the corresponding di-iodidopyrimidine (13) followed by introduction of the amino group may be used to generate iodopyrimidines (14).

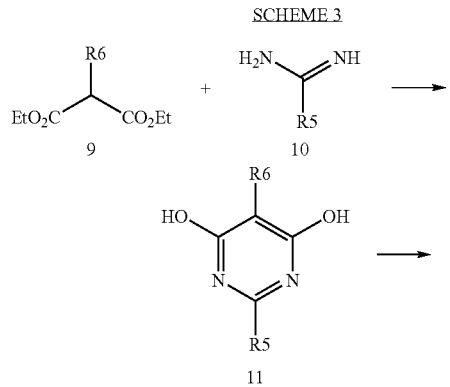

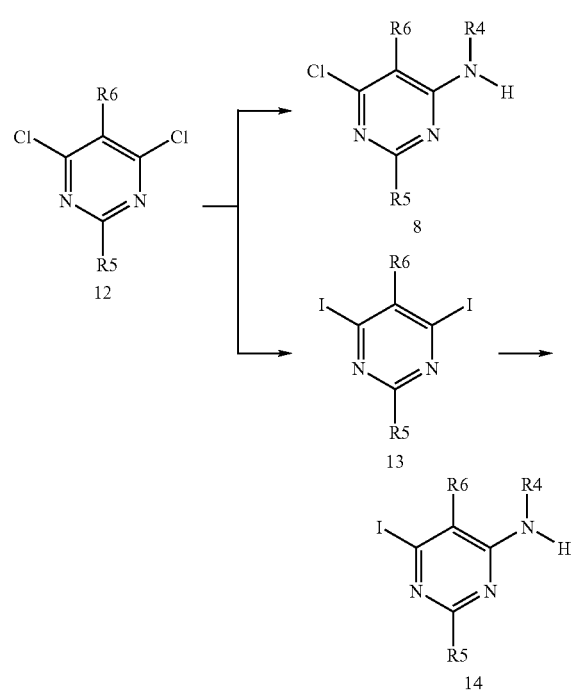

Compounds of Formula I [$X^1$=S, L=S(O)$_n$, L=N(R$^4$), R$^2$=substituted heteroaryl, $X^2$ is =N—, $X^3$ is =C(R$^6$)—; R$^6$ is -L$^3$-NR$^8$R$^9$, L$^3$ is a bond] can be obtained using a variety of procedures known in the literature, such as Scheme 4. These compounds can be prepared by a sequence beginning with conversion of an aminothiazole (3) to a suitable 2-halothiazole (15). Reaction of 13 with an amino-heterocycle such as 8 or 14, optionally in the presence of a base, in a polar aprotic solvent such as THF or DMF, and heat, typically at about 60-100° C., to give adducts of the general structure 16. Subsequent reaction of 16 with a suitable amine, 17, optionally in the presence of a base, in a polar aprotic solvent such as THF or DMF, and heat, typically at about 60-100° C., to give adducts of the general structure 18. In both transformations, the base is preferably a trialkylamine, such as DIEA, or an alkali metal hydride, such as NaH.

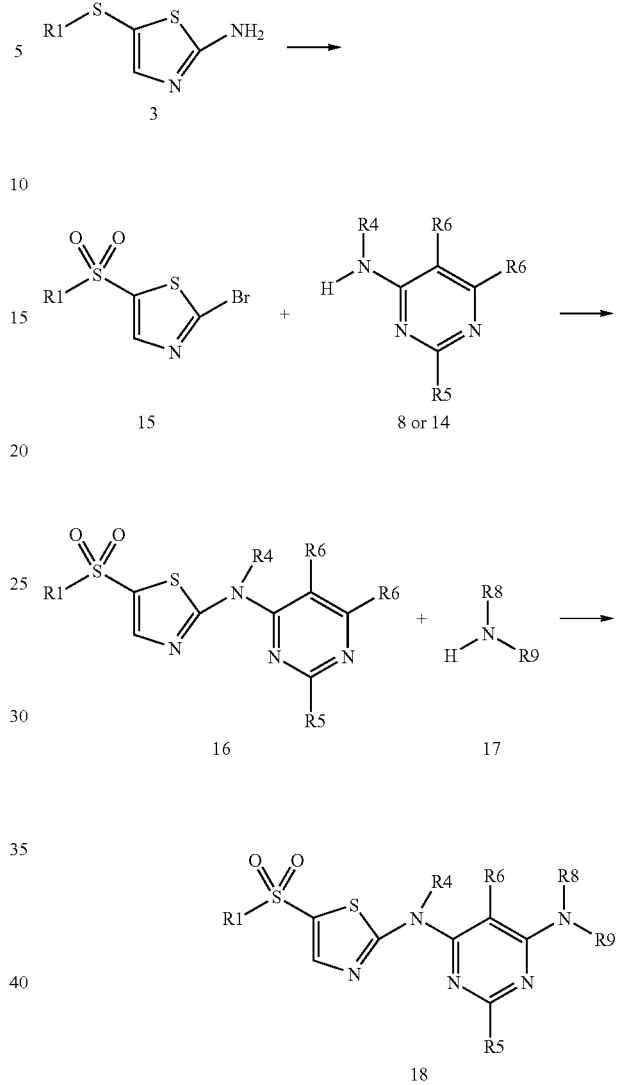

Compounds of Formula I [$X^1$=S, L$^1$=S(O)$_n$, L$^2$=N(R$^4$), R$^2$=substituted heteroaryl, $X^2$ is =N—, $X^3$ is =C(R$^6$)—; R$^6$ is -L$^3$-OR$^7$, L$^3$ is a bond] can be obtained generally using a synthetic sequence such as Scheme 5. These compounds can be prepared by reaction of 16 with a suitable alcohol 19, optionally in the presence of a base, preferably an alkali metal hydride such as NaH, in a polar aprotic solvent such as THF or DMSO, and heat, typically at about 100-150° C., to give adducts of the general structure 20.

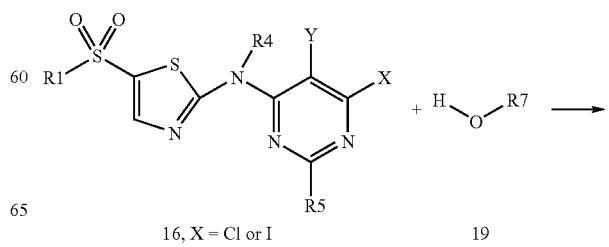

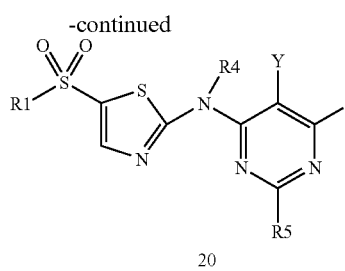

Compounds of Formula I [$X^1$=S, $L^1$=S(O)$_n$, $L^2$=N($R^4$), $R^2$=substituted heteroaryl, $X^2$ is =N—, $X^3$ is =C($R^6$)—; $R^6$ is -$L^3$-$R^7$, $L^3$ is a substituted alkylene, alkenylene, or alkynylene] can be obtained generally using synthetic procedures known in the literature (Gomtsyan, A. et al *J. Med. Chem.* 2002, 45, 3639). As shown in Scheme 6, Sonogashira coupling reaction of 16 with, for example, a terminal acetylene (21) gives adducts of the general structure 22 ($L^3$=alkynylene). Subsequent reduction of the alkynylene, usually under elevated pressure, such as 50-70 psi of hydrogen, using an appropriate catalyst, provides compound of the general structure 23 ($L^3$=alkylene or alkenylene).

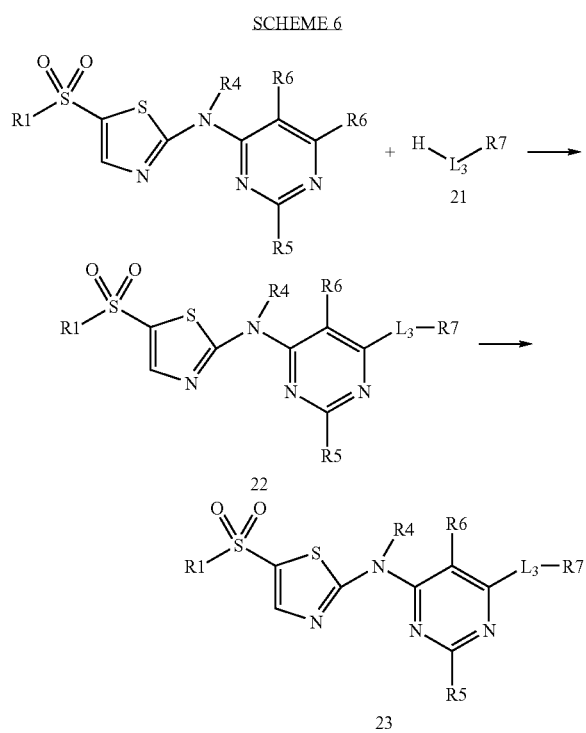

IV. Assays for Blockers of Voltage-Dependent T-Type Calcium Channels

The activity of T-type calcium channels can be assessed using a variety of in vitro assays, including, but not limited to, measuring changes in cellular cation flux, transmembrane potential, and/or cellular electrical currents. Measurement of ionic fluxes can be accomplished by measuring changes in the concentration of the permeant species using, for example, calcium sensitive fluorescent dyes (e.g. FLUO-4), or by tracking the movement of small amounts of an appropriately permeant radioactive tracer (e.g. 45-calcium). A preferred means to determine changes in cellular polarization is by measuring changes in current or voltage with the voltage-clamp and patch-clamp techniques, using the "cell-attached" mode, the "inside-out" mode, the "outside-out" mode, the "perforated patch" mode, the "whole cell" mode, or other means of controlling or measuring changes in transmembrane potential (see, e.g., Ackerman et al., New Engl. J. Med., 336: 1575-1595 (1997)). Whole cell currents are conveniently determined using the standard methodology (see, e.g., Hamill et al., Pflugers. Archiv. 391: 85 (1981). Functional consequences of the test compound on ion flux can be quite varied. Accordingly, any suitable physiological change can be used to assess the influence of a test compound on the channels of this invention. For example, the effects of a test compound can be measured by a toxin-binding assay. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as Ca2+, or cyclic nucleotides.

Antagonists of T-type calcium channels can be tested using recombinant channels, or by examining cells that express native T-type calcium currents (i.e. dorsal ganglion neurons, Todorovic S M, et al (2001) Neuron. 31:75-85). Recombinant T-type calcium channels can be transiently or stably expressed in a host cell which can be mammalian in origin (for example, human embryonic kidney (HEK-293) or Chinese Hamster Ovary (CHO) cells) or in other cell systems like amphibian oocytes or insect cells.

Assays for compounds capable of inhibiting or increasing divalent cation flux through T-type calcium channel proteins can be performed by application of the compounds to a bath solution containing cells expressing functional T-type calcium channels. The compounds are then allowed to contact the cells in the bath. Samples or assays that are treated with a potential T-type calcium channel antagonist are compared to control samples without the test compound, to examine the extent of modulation. Control samples (untreated with inhibitors) are assigned a relative calcium channel activity value of 100. Inhibition of T-type calcium channels is achieved when the calcium channel activity value relative to the control is less than 70%, preferably less than 40%, and still more preferably less than 30% at a concentration of 100 μM, preferably less than 10 μM, and still more preferably less than 1 μM. Generally, the compounds to be tested are present in the range from about 1 μM to about 100 mM, preferably from about 1 nM to about 30 μM. In some embodiments, the compounds to be tested are present in the range from about 1 nM to about 3 μM.

V. Pharmaceutical Compositions for use as Potassium Ion Channel Antagonists

In another aspect, the present invention provides pharmaceutical compositions comprising a pharmaceutically acceptable carrier and an antagonist of the present invention (e.g. a compound of the present invention or a complex of the present invention).

Formulation of the Antagonists

The antagonists of the present invention can be prepared and administered in a wide variety of oral, parenteral and topical dosage forms. Thus, the antagonists of the present invention can be administered by injection, that is, intravenously, intramuscularly, intracutaneously, subcutaneously, intraduodenally, or intraperitoneally. Also, the antagonists described herein can be administered by inhalation, for example, intranasally. Additionally, the antagonists of the present invention can be administered transdermally. Accordingly, the present invention also provides pharmaceutical compositions comprising a pharmaceutically acceptable carrier and either an antagonist, or a pharmaceutically acceptable salt of an antagonist.

For preparing pharmaceutical compositions from the antagonists of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active antagonist. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active antagonist with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

VI. Methods for Decreasing Ion Flow in Calcium Channels

In yet another aspect, the present invention provides a method for decreasing ion flow through a voltage-dependant calcium channel in a cell. The method includes contacting the cell with a calcium channel-closing amount of an antagonist of the present invention.

In an exemplary embodiment, the voltage-dependent calcium channel is a T-type calcium channel.

VII. Method for Treating Conditions Mediated by Calcium Channels

In still another aspect, the present invention provides a method for treating a disease through antagonizing calcium ion flow through calcium channels. An "antagonist," as used herein, means a compound capable of decreasing the flow of ions in a calcium channel relative to the absence of the antagonist.

The antagonists are useful in the treatment of epilepsy, stroke, anxiety, stress-related disorders, brain trauma, Alzheimer's disease, multi-infarct dementia, Korsakoff s disease, neuropathy caused by a viral infection of the brain or spinal cord, amyotrophic lateral sclerosis, convulsions, seizures, Huntington's disease, amnesia, pain transmission, damage to the nervous system resulting from reduced oxygen supply, poison or other toxic substances, muscular dystrophy, hypertension, cardiac arrhythmia, or low sperm count. This method involves administering, to a patient, an effective amount (e.g. a therapeutically effective amount) of an antagonist of the present invention (a compound or complex of the present invention).

Thus, the antagonists provided herein find therapeutic utility via antagonism of calcium channels in the treatment of diseases or conditions. In some embodiments, methods include contacting the cell with a calcium channel-closing amount of an antagonist of the present invention. In some embodiments, the calcium channel is a T-type calcium channel. The cell may be isolated or form part of a organ or organism (e.g. a mammal such as a human).

In therapeutic use for the treatment of neurological conditions, the antagonists utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the antagonist being employed. Determination of the proper dosage for a particular situation is within the skill of the practitioner. Generally, treatment is initiated with smaller dosages, which are less than the optimum dose of the antagonist. Thereafter, the dosage is increased by small increments until the optimum effect under the circumstances is reached. For convenience, the total daily dosage may be divided and administered in portions during the day.

The materials and methods of the present invention are further illustrated by the examples which follow, which are offered to illustrate, but not to limit, the claimed invention. The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the calcium channel agonists are equally applicable to the methods of treating disease states described herein. All publications, patents, and patent applications cited herein are hereby incorporated by reference in their entirety for all purposes.

VIII. Examples

The following examples are provided solely to illustrate the present invention and are not intended to limit the scope of the invention, as described herein. All starting materials were obtained from commercial suppliers and used without further purification, unless otherwise noted. Unless otherwise indicated, all reactions conducted under an inert atmosphere at RT. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck) using an ISCO automated system. Melting points were determined using a Mel-Temp II apparatus and are uncorrected.

$^1$H NMR spectra were recorded on a Varian 300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a Perkin-Elmer SCIEX API-150-EX spectrometer. All mass spectra were taken under electrospray ionization.

Key Intermediate 1 (Int-1A): 2-bromo-5-(3-ethoxy-benzesulfonyl)-thiazole

Part A: A mixture of 3-ethoxythiophenol (10.0 g, 0.065 mol), 2-amino-5-bromothiazole monohydrobromide (17.7 g, 0.068 mol), 1 M aqueous NaOH (200 mL), and THF (200 mL) was stirred at RT for 15 min. The reaction mixture was warmed to 55° C. over 1 h, cooled to RT and concentrated under reduced pressure to remove THF. The residue was partitioned between EtOAc (ca. 500 mL) and water (ca 100 mL), and the layers were separated. The organic phase was washed with saturated aqueous NaCl (1×200 mL), dried (Na$_2$SO$_4$), and concentrated under reduced pressure to give a solid. The solid was triturated with CH$_2$Cl$_2$:hexanes (ca. 10:1) to provide 5-(3-ethoxy-phenylsulfanyl)-thiazol-2-ylamine (13.2 g, 80%) as a light brown solid. LCMS (m/z): 253 (M+H)$^+$ Part B: Copper (II) bromide (12.6 g, 57.0 mmol) was added to a mixture of 5-(3-ethoxy-phenylsulfanyl)-thiazol-2-ylamine (13.0 g, 52.0 mol) and acetonitrile (500 mL). The reaction mixture was cooled to 0° C. and t-butyl nitrite (9.80 mL, 82.0 mmol) was added dropwise. The reaction mixture was stirred at 0° C. for 2 hours and was allowed to warm to RT overnight. The reaction mixture was concentrated under reduced pressure. The residue was purified by flash chromatography, elution with 19:1 hexanes:EtOAc), to give 2-bromo-5-(3-ethoxy-phenylsulfanyl)-thiazole (11.4 g, 70%) as an oil.

Part C: A solution of Oxone® (30.6 g, 0.049 mol) in water (50.0 mL) was added to a solution of 2-bromo-5-(3-ethoxy-phenylsulfanyl)-thiazole (5.25 g, 0.017 mol) in acetone (100 mL) at RT. Saturated aqueous NaHCO$_3$ was added periodically to maintain pH=8. The reaction mixture was stirred at RT for 2 h and concentrated under reduced pressure to remove acetone. The aqueous residue was extracted with EtOAc (2×200 mL). The combined organic layers were washed with saturated aqueous NaCl (1×100 mL), dried. The solid was triturated with hexanes:EtOAc (ca. 19:1) to provide Int-1A (4.40 g, 76%) as a white solid. LCMS (m/z): 348,350 (M+H)$^+$ Using the procedure described above, the following compounds in Table 1 were prepared: Int-1B from 3-(trifluoromethoxy)thiophenol; Int-1C from 3-fluorothiophenol; and Int-1D from 4-fluorothiophenol.

TABLE 1

| | |
|---|---|
| Int-1B | 2-bromo-5-(3-(trifluoro)methoxy-benzenesulfonyl)-thiazole |
| Int-1C | 2-bromo-5-(4-fluoro-benzenesulfonyl)-thiazole |
| Int-1D | 2-bromo-5-(3-fluoro-benzenesulfonyl)-thiazole |

Key Intermediate 2 (Int-2): (6-Chloro-pyrimidin-4-yl)-[5-(3-ethoxy-benzenesulfonyl)-thiazol-2-yl]amine A mixture of 4-amino-6-chloro-pyrimidine (560 mg, 4.30 mmol) and NaH (60% dispersion in mineral oil, 210 mg, 5.25 mmol) in THF (45 mL) was stirred, under Ar, at 0° C. for 30 min. A solution of Int-1 (1.00 g, 2.90 mmol) in THF (10 mL) was added. The reaction mixture was heated at reflux for 4 h and was allowed to cool to RT. The reaction mixture was quenched with water, acidified with 1N aqueous HCl and partitioned with 10% MeOH/CHCl$_3$. The organic phase was separated, dried (Na$_2$SO$_4$), and concentrated under reduced pressure. The residue was purified by flash chromatography, elution with 1-100% EtOAc in hexanes, to give Int-2 (566 mg, 50%) as a yellow solid. LCMS (m/z): 397, 399 (M+H)$^+$ Key Intermediate 3 (Int-3): (6-Chloro-2-methyl-pyrimidin-4-yl)-[5-(3-ethoxy-benzenesulfonyl)-thiazol-2-yl]-amine Part A: A mixture of 4,6-dichloro-2-methylpyrimidine (1.63 g, 10.0 mmol) in NH$_4$OH (35%, 8 mL, 200 mmol) was heated, in a Parr bomb, in an oven at 90° C. overnight. The vessel was cooled to room temperature, the mixture was filtered and the solids were washed with water (3×10 mL). Excess solvent was removed in vacuo to give 4-amino-6-chloro-2-methylpyrimidine (1.17 g, 81%) as an amorphous solid.

Part B: A mixture of 4-amino-6-chloro-2-methylpyrimidine (1.54 g, 10.8 mmol) and NaH (60% dispersion in mineral oil, 540 mg, 13.5 mmol) in THF (120 mL) was stirred, under Ar, at 0° C. for 30 min. A solution of Intl-A (2.61 g, 7.49 mmol) in THF (30 mL) was added. The reaction mixture was heated at reflux overnight and was allowed to cool to RT. The reaction mixture was quenched with water, acidified with 1N aqueous HCl and partitioned with 10% MeOH/CHCl$_3$. The organic phase was separated, dried (Na$_2$SO$_4$), and concentrated under reduced pressure. The residue was purified by flash chromatography, elution with 1-100% EtOAc in hexanes, to give Int-3 (1.80 g, 57%) as a pale yellow solid. LCMS (m/z): 411, 413 (M+H)$^+$ Key Intermediate 4 (Int-4): (6-Chloro-5-fluoro-2-methyl-pyrimidin-4-yl)-[5-(3-ethoxy-benzenesulfonyl)-thiazol-2-yl]-amine Part A: A mixture of sodium metal (1.55 g, 67.4 mmol) and EtOH (15.0 mL, 257 mmol) was stirred at RT until nearly all sodium had reacted. Diethyl fluoromalonate (3.54 mL, 22.4 mmol) was added followed by acetamidine hydrochloride (2.14 g, 22.7 mmol). The reaction mixture was heated at reflux for 3 h, cooled to RT and concentrated under reduced pressure. The residue was diluted with water (ca. 50 mL) and acidified (pH=2) with 6M aqueous HCl, and the mixture was stirred at RT for 1 h as a precipitate formed. The solids were collected by suction filtration and washed with water. Excess solvent was removed in vacuo to give 4,6-dihydroxy-5-fluoro-2-methylpyrimidine (2.08 g, 64%) as a light gray solid. LCMS (m/z): 145 $(M+H)^+$ Part B: A mixture of 4,6-dihydroxy-5-fluoro-2-methylpyrimidine (2.00 g, 13.9 mmol), phosphorous oxychloride (15.0 mL, 161 mmol), and N,N-dimethylaniline (2.00 mL, 15.8 mmol) was heated at reflux for 2 h. The reaction mixture was cooled to RT and concentrated under reduced press. The residue was poured onto ice and allowed to warm to RT as a ppt formed. The solids were collected by suction filtration, washed with water, and air-dried at RT for 1 h to give 4,6-dichloro-5-fluoro-2-methylpyrimidine (1.56 g, 62%) as a tan solid. LCMS (m/z): 181,183 $(M+H)^+$ Part C: A mixture of 4,6-dichloro-5-fluoro-2-methylpyrimidine (1.55 g, 8.56 mmol), ammonium hydroxide (35%, 10.0 mL, 257 mmol), and MeOH (1.00 mL) was heated, in a sealed tube, at 70° C. for 2 h. The reaction mixture was cooled to RT, and a precipitate was formed. The reaction mixture was diluted with water (ca. 10 mL) and was stirred 30 min. The solids were collected by suction filtration, washed with water and air-dried to give 4-amino-6-chloro-5-fluoro-2-methylpyrimidine (845 mg, 61%) as a tan solid. LCMS (m/z): 162,164 $(M+H)^+$ Part D: A mixture of 4-amino-6-chloro-5-fluoro-2-methylpyrimidine (840 mg, 5.20 mmol) and NaH (60% dispersion in mineral oil, 229 mg, 5.73 mmol) in DMF (20.0 mL) was stirred, under Ar, at RT for 15 min. A solution of Intl-A (1.81 g, 5.20 mmol) in DMF (5.0 mL) was added, and the reaction mixture was stirred at RT 15 min. Additional NaH (60% dispersion in mineral oil, 210 mg, 5.25 mmol) was added and the reaction mixture was heated at 60° C. for 30 min. Additional NaH (60% dispersion in mineral oil, 210 mg, 5.25 mmol) was added and the reaction mixture was heated at 60° C. for 1 h. The reaction mixture was cooled to RT and was partitioned between EtOAc (ca. 150 mL) and water (ca. 50 mL). The layers were separated, and the organic layer was washed with saturated aqueous NaCl (1×100 mL), dried (Na$_2$SO$_4$), and concentrated under reduced pressure to give an oil. The oil was triturated with CH$_2$Cl$_2$:hexanes (9:1) to give the Int-4 (1.28 g, 57%) as a pale yellow solid. LCMS (m/z): 429, 431 $(M+H)^+$ Key Intermediate 5 (Int-5): (6-Chloro-2-trifluoromethyl-pyrimidin-4-yl)-[5-(3-ethoxy-benzenesulfonyl)-thiazol-2-yl]-amine A mixture of 4-amino-6-chloro-2-trifluoromethyl-pyrimidine [(Inoue, S. et al, *J. Org. Chem.*, 1961, 26, 4504) 185 mg, 0.94 mol] and NaH (60% dispersion in mineral oil, 40 mg, 1.0 mmol) in DMF (4.0 mL) was stirred, under Ar, at RT for 30 min. A solution of Intl-A (326 mg, 0.94 mmol) in DMF (2.0 mL) was added. The reaction mixture was stirred at RT for 30 min and was heated at 55° C. for 1 h. Additional NaH (60% dispersion in mineral oil, 20 mg, 0.05 mmol) was added, and the reaction mixture was heated at 55° C. overnight. Additional NaH (60% dispersion in mineral oil, 20 mg, 0.05 mmol) was added, and the reaction mixture was heated at 55° C. for 1 h. The reaction mixture was cooled to RT and partitioned between EtOAc (ca. 100 mL) and water (ca. 25 mL). The layers were separated and the organic phase was washed with saturated aqueous NaCl (1×100 mL), dried (Na$_2$SO$_4$), and concentrated under reduced pressure to give an oil. This oil was purified by flash chromatography, elution with 25-75% EtOAc in hexanes, to give Int-5 (182 mg, 42%) as a foam. LCMS (m/z): 465, 467 $(M+H)^+$ Key Intermediate 6 (Int-6): [5-(3-Ethoxy-benzenesulfonyl)-thiazol-2-yl]-(6-iodo-2-methyl-pyrimidin-4-yl)-amine Part A: Hydrogen iodide (3.5 M in water, 30.0 nL) was added to a solution of 4,6-dichloro-2-methylpyrimidine (5.00 g, 0.03 mol) and sodium iodide (23.0 g, 0.15 mol) in acetone (150 mL) at RT for 2 h. The reaction mixture was stirred at RT for 16 h, poured onto ice:water [(ca. 1:1) approx. 250 mL] and allowed to warm to RT. The solids were collected by suction filtration, washed with water, and air-dried to give 4,6-diodo-2-methylpyrimidine (9.80 g, 92%) as an off-white solid. LCMS (m/z): 347 $(M+H)^+$ Part B: A suspension of 4,6-diodo-2-methylpyrimidine (1.83 g, 5.29 mmol) in ammonia (2 M solution in EtOH, 10 mL) was heated, in a sealed tube, at 100° C. for 18 h. The reaction mixture was cooled to RT and concentrated under reduced pressure. The solid residue was washed with EtOAc and the filtrate was concentrated under reduced pressure to give 4-amino-6-diodo-2-methylpyrimidine (1.05 g, 84%) as a pale yellow solid. LCMS (m/z): 235 $(M+H)^+$ Part C: A mixture of 4-amino-6-diodo-2-methylpyrimidine (500 mg, 2.13 mmol) and NaH (60% dispersion in mineral oil, 170 mg, 4.25 mmol) in DMF (15 mL) was stirred at RT for 30 min. A solution of Intl-A (741 mg, 2.13 mol) in DMF (7 mL) was added, and the reaction mixture was stirred at RT for 1 h. The reaction mixture was poured into EtOAc (ca. 100 mL) and water (ca. 25 mL), 1M aqueous HCl was added to give pH=7, and the layers were separated. The organic layer was dried (Na$_2$SO$_4$) and concentrated under reduced pressure. The residue was purified by flash chromatography, elution with 40-75% EtOAc in hexanes, to give Int-6 (710 mg, 66%) as an off-white solid. LCMS (m/z): 503 $(M+H)^+$ Example 1

2-(3,4-Dimethoxy-phenyl)-N-[5-(3-ethoxy-benzenesulfonyl)-thiazol-2-yl]-acetamide Part A: 3-Ethoxythiophenol (0.25 mL, 1.80 mmol) was added to a mixture of 2-(3,4-dimethoxyphenyl)-N-[5-(3-bromothiazol-2-yl]-acetamide (581 mg, 1.63 mmol), potassium carbonate (340 mg, 2.40 mol) in DMF (8.00 mL). The reaction mixture was heated at 110° C. for 2 hours, was poured onto ice, and was allowed to warm to room temperature. The reaction mixture was extracted with EtOAc (3×50 mL). The combined organic layers were washed with saturated aqueous NaCl (2×100 mL), dried (Na$_2$SO$_4$), and concentrated under reduced pressure. The residue was purified by flash chromatography, elution with 19:1 hexanes:EtOAc), to give 2-(3,4-Dimethoxyphenyl)-N-[5-(3-ethoxy-benzenesulfanyl)-thiazol-2-yl]-acetamide (415 mg, 59%) as a pale yellow amorphous solid. LCMS (m/z): 431 $(M+H)^+$ Part B: A solution of Oxone® (2.00 g, 3.00 mmol) in water (8.00 mL) was added to a solution of the compound obtained in Part A (415 mg, 0.96 mmol) in acetone (25.0 mL) at RT. Saturated aqueous NaHCO$_3$ was added periodically to maintain pH=8. The reaction mixture was stirred at RT over 72 h and concentrated under reduced pressure. The residue was purified by flash chromatography, elution with 1:1 hexanes:

EtOAc), to give the title compound (296 mg, 64%) as a white amorphous solid. LCMS (m/z): 463 (M+H)+

Example 2

N-(2-Pyrrolidin-1-ethyl)-N'-[5-(3-ethoxy-benzenesulfonyl)-thiazol-2-yl]-pyrimidine-4,6-diamine. A mixture of Int-2 (250 mg, 0.63 mmol), N-(2-aminoethyl)pyrrolidine (0.40 mL, 3.0 mmol) and Et$_3$N (0.19 mL, 1.40 mmol) in 1,4-Dioxane (4 mL) was heated at 90° C. overnight. The reaction mixture was concentrated under reduced pressure. The residue was purified by flash chromatography, elution with 0-20% CMA (CHCl$_3$:MeOH:NH$_4$OH; 80:18:2) in CHCl$_3$ to give the title compound (175 mg, 58%) as an off-white solid. LCMS (m/z): 475 (M+H)+

The procedure described above for Example 2 was used to prepare the compounds below in Table. 2:

TABLE 2

| Example 3 | N-(2-Dimethylamino-ethyl)-N'-[5-(3-ethoxy-benzenesulfonyl)-thiazol-2-yl]-pyrimidine-4,6-diamine |
| --- | --- |
| Example 4 | N-[5-(3-Ethoxy-benzenesulfonyl)-thiazol-2-yl]-N'-(2-methoxy-ethyl)-pyrimidine-4,6-diamine |
| Example 5 | N-[5-(3-Ethoxy-benzenesulfonyl)-thiazol-2-yl]-N'-(2-methoxy-ethyl)-N'-methyl-pyrimidine-4,6-diamine |

Example 6

N-(2-Amino-2-methyl-propyl)-N'-[5-(3-ethoxy-benzenesulfonyl)-thiazol-2-yl]-2-methyl-pyrimidine-4,6-diamine. TFA salt. A mixture of Int-3 (600 mg, 1.3 mmol), 1,2-Diamino-2-methylpropane (0.30 mL, 3.0 mmol) and N,N-Diisopropylethylamine (0.51 mL, 2.9 mmol) in 1,4-Dioxane (9 mL) was heated, in a sealed tube, at 100° C. overnight. Additional 1,2-diamino-2-methylpropane (0.20 mL, 2.0 mmol) and N,N-diisopropylethylamine (0.34 mL, 2.0 mmol) of DIEA were added, and the reaction mixture was heated at 100° C. for 4 h. The reaction mixture was concentrated under reduced pressure. The residue was purified by reverse phase chromatography to give the title compound (574 mg, 70%), as a yellow solid. LCMS (m/z): 463 (M+H)+

The procedure described above for Example 6 was used to prepare the compounds below in Table 3.:

TABLE 3

| Example 7 | N-[5-(3-ethoxy-benzenesulfonyl)-thiazol-2-yl]-N'-(2-methoxy-ethyl)-2-methyl-pyrimidine-4,6-diamine |
| --- | --- |
| Example 8 | N-(2-Dimethylamino-ethyl)-N'-[5-(3-ethoxy-benzenesulfonyl)-thiazol-2-yl]-2-methyl-pyrimidine-4,6-diamine |
| Example 9 | N-[5-(3-ethoxy-benzenesulfonyl)-thiazol-2-yl]-2-methyl-N'-(2-pyrrolidin-1-yl-ethyl)-pyrimidine-4,6-diamine |
| Example 10 | N-[5-(3-ethoxy-benzenesulfonyl)-thiazol-2-yl]-2-methyl-N'-(R)-(pyrrolidin-3-yl-ethyl)-pyrimidine-4,6-diamine |
| Example 11 | N-(1-Amino-cyclohexylmethyl)-N'-[5-(3-ethoxy-benzenesulfonyl)-thiazol-2-yl]-2-methyl-pyrimidine-4,6-diamine |

Example 12

N-[5-(3-Ethoxy-benzenesulfonyl)-thiazol-2-yl]-5-fluoro-2-methyl-N'-(2-pyrrolidin-1-yl-ethyl)-pyrimidine-4,6-diamine. TFA salt. A mixture of Int-4 (35 mg, 0.08 mmol), N-(2-aminoethyl)pyrrolidine (0.02 mL, 0.20 mmol) and N,N-Diisopropylethylamine (0.03 mL, 0.02 mmol) in DMSO (0.50 mL) was heated at 130° C. overnight. The reaction mixture was concentrated under reduced pressure. The residue was purified by reverse phase chromatography to give the title compound (12 mg, 23%) as a white solid. LCMS (m/z): 507 (M+H)+

The procedure described above for Example 12 was used to prepare the compounds below in Table 4.

TABLE 4

| Example 13 | N-[5-(3-ethoxy-benzenesulfonyl)-thiazol-2-yl]-5-fluoro-N'-(2-methoxy-ethyl)-2,N'-dimethyl-pyrimidine-4,6-diamine |
| --- | --- |
| Example 14 | N-(2-Amino-2-methyl-propyl)-N'-[5-(3-ethoxy-benzenesulfonyl)-thiazol-2-yl]-5-fluoro-2-methyl-pyrimidine-4,6-diamine |
| Example 15 | N-[5-(3-ethoxy-benzenesulfonyl)-thiazol-2-yl]-5-fluoro-N'-(2-methoxy-ethyl)-2-methyl-N-(3'-morpholin-4-yl-propyl)-pyrimidine-4,6-diamine |

Example 16

N-[5-(3-Ethoxy-benzenesulfonyl)-thiazol-2-yl]-N'-(2-pyrrolidin-1-yl-ethyl)-2-trifluoromethyl-pyrimidine-4,6-diamine. TFA salt. A mixture of Int-5 (35 mg, 0.08 mmol), N-(2-aminoethyl)pyrrolidine (0.02 mL, 0.20 mmol) and Et$_3$N (0.02 mL, 0.02 mmol) in 1,4-dioxane (0.50 mL) was heated at 90° C. overnight. The reaction mixture was concentrated under reduced pressure. The residue was purified by reverse phase chromatography to give the title compound (27 mg, 55%) as a white solid. LCMS (m/z): 543 (M+H)+

The procedure described above for Example 16 was used to prepare the compounds below in Table 5.

TABLE 5

| Example 17 | N-[5-(3-ethoxy-benzenesulfonyl)-thiazol-2-yl]-N'-(2-methoxy-ethyl)-2-trifluoromethyl-pyrimidine-4,6-diamine |
| --- | --- |
| Example 18 | N-(2-Amino-2-methyl-propyl)-N'-[5-(3-ethoxy-benzenesulfonyl)-thiazol-2-yl]-2-trifluoromethyl-pyrimidine-4,6-diamine |
| Example 19 | N-(2-Dimethylamino-ethyl)-N'-[5-(3-ethoxy-benzenesulfonyl)-thiazol-2-yl]-2-trifluoromethyl-pyrimidine-4,6-diamine |

Example 20

[5-(3-Ethoxy-benzenesulfonyl)-thiazol-2-yl]-[2-methyl-6-(2-pyrrolidin-1-yl-ethoxy)-pyrimidin-4-yl]-amine-TFA salt. Sodium hydride (97% dispersion in mineral oil, 370 mg, 15.0 mmol) was added to a solution of N-β-hydroxyethylpyrrolidine (850 mg, 7.40 mmol) in DMSO (7 mL) at RT. After 5 min, Added Int-3 (473 mg, 1.15 mmol) was added, and the reaction mixture was heated at 130° C. for 30 min. The reaction mixture was purified directly by reverse phase chromatography, and the product was lyophilized to give the title cmpd (374 mg, 65%) as a white powder. LCMS (m/z): 490 (M+H)+

The procedure described above for Example 20 was used to prepare the compounds below in Table 6.

TABLE 6

| Example 21 | N-[5-(3-ethoxy-benzenesulfonyl)-thiazol-2-yl]-[2-methyl-((6R)-1-pyrrolidin-2-yl-methoxy)pyrimidin-4-yl]-amine |
|---|---|
| Example 22 | N-[5-(3-ethoxy-benzenesulfonyl)-thiazol-2-yl]-[2-methyl-6-(pyrrolidin-3-yl oxy)pyrimidin-4-yl]-amine |
| Examle 23 | N-[5-(3-ethoxy-benzenesulfonyl)-thiazol-2-yl]-[6-(2-methoxy-ethoxy)-2-methyl-pyrimidin-4-yl]-amine |

Example 24

[5-(3-Ethoxy-benzenesulfonyl)-thiazol-2-yl]-[5-fluoro-2-methyl-6-(2-pyrrolidin-1-yl-ethoxy)-pyrimidin-4-yl]-amine-TFA salt. Sodium hydride (97% dispersion in mineral oil, 200 mg, 8.30 mmol) was added to a solution of Int-4 (269 mg, 6.27 mmol) and N-β-hydroxyethylpyrrolidine (0.37 mL, 3.20 mmol) in DMSO (3 mL). The reaction mixture was heated at 130° C. for 30 min. The reaction mixture was purified directly by reverse phase chromatography, and the product was lyophilized to give the title cmpd (118 mg, 35%) as a white powder. LCMS (m/z): 508 (M+H)$^+$ The procedure described above for Example 24 was used to prepare the compounds below in Table 7.

TABLE 7

| Example 25 | N-[5-(3-ethoxy-benzenesulfonyl)-thiazol-2-yl]-[5-fluoro-6-(2-methoxy-ethoxy)-2-methyl-pyrimidin-4-yl]-amine |
|---|---|
| Example 26 | [6-(2-Cyclopentyl-ethoxy)-5-fluoro-2-methyl-pyrimidn-4-yl]-[5-(3-ethoxy-benzenesulfonyl)-thiazol-2-yl]-amine |
| Example 27 | [6-(2-Dimethylamino-ethoxy)-5-fluoro-2-methyl-pyrimidin-4-yl]-[5-(3-ethoxy-benzenesulfonyl)-thiazol-2-yl]-amine |

Example 28

[6-(2-Dimethylamino-ethoxy)-2-trifluormethyl-pyrimidin-4-yl]-[5-(3-Ethoxy-benzenesulfonyl)-thiazol-2-yl]-amine-TFA salt. Sodium hydride (97% dispersion in mineral oil, 32 mg, 1.3 mmol) was added to a solution of Int-5 (61 mg, 0.13 mmol) and N,N-dimethylaminoethanol (0.07 mL, 0.70 mmol) in DMSO (1 mL). The reaction mixture was heated at 130° C. for 30 min. The reaction mixture was purified directly by reverse phase chromatography, and the product was lyophilized to give the title cmpd (6 mg, 8%) as a tan powder. LCMS (m/z): 518 (M+H)$^+$

Example 29

[5-(3-Ethoxy-benzenesulfonyl)-thiazol-2-yl]-[6-(3-methoxy-prop-1-ynyl)-2-methyl-pyrimidin-4-yl]-amine. Copper (I) iodide (2.0 mg, 0.01 mmol) was added to a solution of Int-6 (100 mg, 0.20 mol), methyl propargyl ether (0.02 mL, 0.024 mmol), and Et$_3$N (0.40 mL, 2.9 mmol) in acetonitrile (2.0 mL) under Ar. Bis(triphenylphosphine)palladium(II) chloride (7.0 mg, 0.01 mol) was added, and the reaction mixture was stirred at RT for 18 h. The reaction mixture was filtered thru Celite using EtOAc (ca. 50 mL), and the filtrate was concentrated under reduced pressure to give an oil. This oil was purified by flash chromatography, elution with 45-90% EtOAc in hexanes, to give the title compound (41 mg, 46%) of as an off-white solid. LCMS (m/z): 445 (M+H)$^+$ The procedure described above for Example 29 was used to prepare the compounds below in Table 8.

TABLE 8

| Example 30 | (3-{6-[5-(3-Ethoxy-benzenesulfonyl)-thiazol-2ylamino]-2-methyl-pyrimidin-4-yl}-prop-2-ynyl)-methyl-carbamic acid tert-butyl ester |
|---|---|
| Example 31 | (3-{6-[5-(3-Ethoxy-benzenesulfonyl)-thiazol-2ylamino]-2-methyl-pyrimidin-4-yl}-1,1-dimethyl-prop-2-ynyl)-methyl-carbamic acid tert-butyl ester |

Example 32

[5-(3-Ethoxy-benzenesulfonyl)-thiazol-2-yl]-[6-(3-methoxy-propyl)-2-methyl-pyrimidin-4-yl]-amine. A mixture of [5-(3-Ethoxy-benzenesulfonyl)-thiazol-2-yl]-[6-(3-methoxy-prop-1-ynyl)-2-methyl-pyrimidin-4-yl]-amine (32.0 mg, 0.072 mol) and Pd—C (10%, 2.0 mg) in THF (1.00 mL) and EtOAc (1.00 mL) was stirred under H$_2$ (70 psi, Parr) for 30 min. The reaction mixture was filtered through Celite using EtOAc (ca. 50 mL). The filtrate concentrated under reduced pressure to give the title compound (30 mg, 93%) as an off-white solid. LCMS (m/z): 449 (M+H)$^+$ The procedure described above for Example 32 was used to prepare the compounds below in Table 9.

TABLE 9

| Example 33 | (3-{6-[5-(3-Ethoxy-benzenesulfonyl)-thiazol-2ylamino]-2-methyl-pyrimidin-4-yl}-propyl)-methyl-carbamic acid tert-butyl ester |
|---|---|
| Example 34 | (3-{6-[5-(3-Ethoxy-benzenesulfonyl)-thiazol-2ylamino]-2-methyl-pyrimidin-4-yl}-1,1-dimethyl-propyl)-carbamic acid tert-butyl ester |

Example 35

[5-(3-Ethoxy-benzenesulfonyl)-thiazol-2-yl]-[6-(3-methylamino)propyl)-2-methyl-pyrimidin-4-yl]-amine-HCl salt. A mixture of [5-(3-Ethoxy-benzenesulfonyl)-thiazol-2-yl]-[6-(3-(BOC-amino)lpropyl)-2-methyl-pyrimidin-4-yl]-amine (32.0 mg, 0.058 mol) and HCl (4 Molar solution in 1,4-dioxane, 2.0 mL) was stirred) for 2 h. The reaction mixture was concentrated under reduced pressure to give the title compound (27 mg, 95%) as an off-white solid. LCMS (m/z): 485 (M+H)$^+$ The procedure described above for Example 35 was used to prepare the compounds below in table 10.

TABLE 10

| Example 36 | [6-(3-Amino-3-methyl-butyl)-2-methyl-pyrimidin-4-yl]-[5-(3-ethoxy-benzenesulfonyl)-thiazol-2yl]-amine |
|---|---|

Activity Assay

T-type calcium channel inhibitory activity of some compounds of the invention was evaluated using both fluorometric as well as electrophysiological measurement methodologies, which are known to those skilled in the art.

Fluorescence measurement of changes in intracellular calcium due to entry of calcium through T-type calcium channels was assessed using calcium sensitive fluorescent dyes Fluo-4 and Fluo-3. In brief, cells natively expressing T-type channels or HEK-293 cells transiently or stably expressing recombinant mammalian T-type calcium channels grown in 96-well tissue culture plates in DMEM/High glucose, Hyclone, Fetal Bovine Serum (10%), and 2 mM sodium pyruvate 2 mM (and for cells lines recombinantly expressing T-type calcium channels, G418@400 mg/liter) were loaded with 4 μM Fluo-4 made up in Earls Balanced Salt Solution (EBSS). After incubation for 30 minutes at room temperature, cells were washed with low calcium (0.5 mM) EBSS to remove extracellular Fluo-4. Baseline fluorescence was measured in a FLIPR (FLuorescence Image Plate Reader) (Molecular Devices Inc) after applying test compounds at desired concentration for 5-10 minutes. The effect of test compound on calcium entry was assessed by monitoring changes in Fluo-4 fluorescence following an elevation of extracellular calcium concentration from 0.5 mM to 5 mM.

Electrophysiological measurements of test compound induced changes in T-type calcium channel activity were assessed as follows. Native cells natively expressing T-type channels or HEK-293 cells transiently or stably expressing recombinant mammalian T-type calcium channels were grown in DMEM/High glucose, Hyclone, Fetal Bovine Serum (10%), 2 mM sodium pyruvate 2 mM (and for cells lines recombinantly expressing T-type calcium channels, G418@400 mg/liter) on glass coverslips in 35 mm tissue culture dishes. Experiments were performed by placing T-type calcium channels expressing cells in a recording chamber perfused with EBSS (which contains (in mM): 132 NaCl, 5.4 KCl, 1.8 CaCl2, 0.8 MgCl2, 10 Hepes, 5 glucose, pH 7.4 with NaOH) on the stage of an inverted microscope. Electrical currents were measured using the whole cell configuration of the patch clamp technique (Axopatch 200B, Axon Instruments (Molecular Devices) (see Hamill et al (1981) PFugers Arch, 1981 391:85-100) using 2-2.5 MOhm resistance glass pipettes filled with 135 CsF, 5 CsCl, 5 NaCl, 5 EGTA, 10 HEPES, pH 7.3 with CsOH, Osmolarity ~288 mOsm. Test compound effects were typically assessed under conditions in which approximately half of the available channels were inactivated either by an 8 second conditioning depolarization from a holding potential of −100 mV to a potential ranging from −70 mV to −60 mV or by continually holding the membrane potential at −70 mV. Test compounds were assessed for their ability to reduce the amplitude of the inward T-type calcium current elicited by a 100 ms step depolarization −20 or −30 mV.

Results are presented in Table 11 below.

TABLE 11

| Example | Activity |
|---------|----------|
| 1 | +++ |
| 2 | +++ |
| 3 | +++ |
| 4 | ++ |
| 5 | ++ |
| 6 | +++ |
| 7 | ++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |

TABLE 11-continued

| Example | Activity |
|---------|----------|
| 21 | +++ |
| 22 | +++ |
| 23 | +++ |
| 24 | +++ |
| 25 | +++ |
| 26 | + |
| 27 | +++ |
| 28 | +++ |
| 29 | ++ |
| 30 | +++ |
| 31 | +++ |
| 32 | +++ |
| 35 | +++ |
| 36 | +++ |

Activity refers to inhibition of T-type calcium channels, where "+" is 10 μM < IC50 ≦ 1 mM; "++" is 1 μM < IC50 < 10 μM; and "+++" is 1 nM < IC50 < 1 μM.

What is claimed is:
1. A compound having the formula

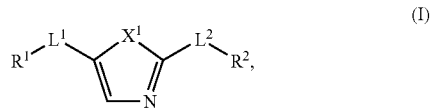

(I)

wherein
$X^1$ is —S—;
$R^1$ is substituted or unsubstituted cycloalkyl, substituted aryl, or substituted heteroaryl, wherein the substituted aryl or substituted heteroaryl is exclusively substituted with one to three substituents selected from the group consisting of unsubstituted —OR' and halogen groups, wherein R' is hydrogen or alkyl;
$R^2$ has the formula:

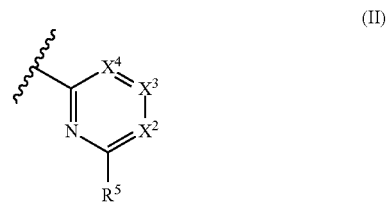

(II)

wherein
$X^2$ and $X^3$ are independently =N— or =C($R^6$)—, wherein $X^3$ is =C($R^6$)— when $X^2$ is =N;
$X^4$ is =C($R^6$)—;
$R^5$ and $R^6$ are independently hydrogen, halogen, —$CF_3$, -$L^3$-$R^7$, -$L^3$-$OR^7$, -$L^3$-$NR^8R^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^3$ is a bond or substituted or unsubstituted alkylene; and
$R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein an $R^8$ and an $R^9$ are optionally joined with the nitrogen to which they are attached to form a substituted or unsubstituted heterocycloalkyl, or substituted or unsubstituted heteroaryl, wherein two $R^7$ substituents are optionally joined with the oxygen to which they are attached to form a substituted or unsubstituted heterocycloalkyl, and wherein an $R^8$ and an $R^7$ are optionally joined with the nitrogen and oxygen to which they are attached, respectively, to form a substituted or unsubstituted heterocycloalkyl, or substituted or unsubstituted heteroaryl;

$L^1$ is —S(O)$_2$— and $L^2$ is —N(R$^4$)—;

wherein $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a pharmaceutically acceptable salt of the compound, wherein the compound is an antagonist of a calcium channel.

2. The compound of claim 1, wherein $R^1$ is phenyl exclusively substituted with one to three substituents selected from the group consisting of unsubstituted —OR' and halogen groups, wherein R' is hydrogen or alkyl.

3. The compound of claim 1, wherein $R^2$ is substituted or unsubstituted pyridinyl, or substituted or unsubstituted pyrimidinyl.

4. The compound of claim 1, wherein
$R^1$ is substituted aryl or substituted heteroaryl, wherein the substituted aryl or substituted heteroaryl is exclusively substituted with one to three substituents selected from the group consisting of unsubstituted —OR' and halogen groups,
wherein R' is hydrogen or alkyl;
$R^2$ is substituted or unsubstituted pyridinyl or pyrimidinyl;
$L^1$ is —S(O)$_2$—;
$L^2$ is —N(R$^4$)—; and
$R^4$ is hydrogen, substituted or unsubstituted alkyl, or substituted or unsubstituted aryl.

5. The compound of claim 1, wherein $L^3$ is a bond, or unsubstituted alkylene.

6. The compound of claim 1, wherein $L^3$ is a bond, or unsubstituted $C_1$-$C_8$ alkylene.

7. The compound of claim 6, wherein said unsubstituted $C_1$-$C_8$ alkylene comprises an alkynylene linking moiety.

8. The compound of claim 1, wherein $R^6$ is -$L^3$-NR$^8$R$^9$, wherein
$L^3$ is a bond;
$R^9$ is hydrogen; and
$R^8$ is substituted or unsubstituted alkyl, or substituted or unsubstituted heteroalkyl.

9. The compound of one of claims 5, 6, 7 and 8, wherein
$R^1$ is substituted aryl or substituted heteroaryl, wherein the substituted aryl or substituted heteroaryl is exclusively substituted with one to three substituents selected from the group consisting of unsubstituted —OR' and halogen groups, wherein R' is hydrogen or alkyl; and
$R^5$ is hydrogen, halogen, substituted or unsubstituted alkyl, or substituted or unsubstituted aryl.

10. The compound of claim 1, wherein $R^4$ is hydrogen, —CF$_3$, unsubstituted alkyl, or unsubstituted heterocycloalkyl.

11. The compound of claim 1, having the formula

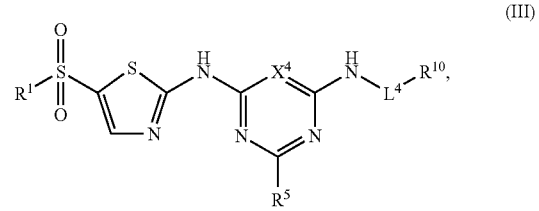

(III)

wherein,
$L^4$ is a bond or substituted or unsubstituted alkylene; and
$R^{10}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

12. The compound of claim 11, wherein $L^4$ is unsubstituted alkylene.

13. The compound of claim 11, wherein $R^1$ is substituted phenyl.

14. The compound of claim 1, wherein $R^6$ is hydrogen.

15. A method of treating a disorder or condition through modulation of a voltage-dependent calcium channel, said method comprising administering to a subject in need of such treatment, an effective amount of a compound of claim 1, wherein said disorder or condition is epilepsy or pain transmission.

16. The method of claim 15, wherein said disorder or condition is epilepsy.

17. A composition comprising a pharmaceutically acceptable excipient and a compound of claim 1.

18. The method of claim 15, wherein said disorder or condition is pain transmission.

19. The compound of claim 1 having the formula:

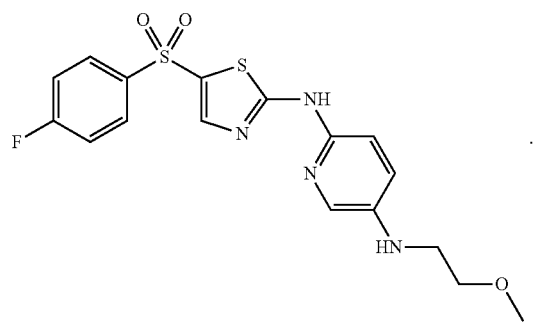

20. A method of treating pain, said method comprising administering to a subject in need of such treatment, an effective amount of a compound of claim 1.

21. The compound of claim 1, wherein the compound is selected from the group consisting of:
N-(2-Pyrrolidin-1-ethyl)-N'-[5-(3-ethoxy-benzenesulfonyl)-thiazol-2-yl]-pyrimidine-4,6-diamine;
N-(2-Dimethylamino-ethyl)-N'-[5-(3-ethoxy-benzenesulfonyl)-thiazol-2-yl]-pyrimidine-4,6-diamine;
N-[5-(3-Ethoxy-benzenesulfonyl)-thiazol-2-yl]-N'-(2-methoxy-ethyl)-pyrimidine-4,6-diamine;
N-[5-(3-Ethoxy-benzenesulfonyl)-thiazol-2-yl]-N'-(2-methoxy-ethyl)-N'-methyl-pyrimidine-4,6-diamine;

N-(2-Amino-2-methyl-propyl)-N'-[5-(3-ethoxy-benzenesulfonyl)-thiazol-2-yl]-2-methyl-pyrimidine-4,6-diamine;
N-[5-(3-ethoxy-benzenesulfonyl)-thiazol-2-yl]-N'-(2-methoxy-ethyl)-2-methyl-pyrimidine-4,6-diamine;
N-(2-Dimethylamino-ethyl)-N'-[5-(3-ethoxy-benzenesulfonyl)-thiazol-2-yl]-2-methyl-pyrimidine-4,6-diamine;
N-[5-(3-ethoxy-benzenesulfonyl)-thiazol-2-yl]-2-methyl-N'-(2-pyrrolidin-1-yl-ethyl)-pyrimidine-4,6-diamine;
N-[5-(3-ethoxy-benzenesulfonyl)-thiazol-2-yl]-2-methyl-N'-(R)-(pyrrolidin-3-yl-ethyl)-pyrimidine-4,6-diamine;
N-(1-Amino-cyclohexylmethyl)-N'-[5-(3-ethoxy-benzenesulfonyl)-thiazol-2-yl]-2-methyl-pyrimidine-4,6-diamine;
N-[5-(3-Ethoxy-benzenesulfonyl)-thiazol-2-yl]-5-fluoro-2-methyl-N'-(2-pyrrolidin-1-yl-ethyl)-pyrimidine-4,6-diamine;
N-[5-(3-ethoxy-benzenesulfonyl)-thiazol-2-yl]-5-fluoro-N'-(2-methoxy-ethyl)-2, N'-dimethyl-pyrimidine-4,6-diamine;
N-(2-Amino-2-methyl-propyl)-N'-[5-(3-ethoxy-benzenesulfonyl)-thiazol-2-yl]-5-fluoro-2-methyl-pyrimidine-4,6-diamine;
N-[5-(3-ethoxy-benzenesulfonyl)-thiazol-2-yl]-5-fluoro-N'-(2-methoxy-ethyl)-2-methyl-N-(3'-morpholin-4-yl-propyl)-pyrimidine-4,6-diamine;
N-[5-(3-Ethoxy-benzenesulfonyl)-thiazol-2-yl]-N'-[2-pyrrolidin-1-yl-ethyl]-2-trifluoromethyl-pyrimidine-4,6-diamine;
N-[5-(3-ethoxy-benzenesulfonyl)-thiazol-2-yl]-N'-(2-methoxy-ethyl)-2-trifluoromethyl-pyrimidine-4,6-diamine;
N-(2-Amino-2-methyl-propyl)-N'-[5-(3-ethoxy-benzenesulfonyl)-thiazol-2-yl]-2-trifluoromethyl-pyrimidine-4,6-diamine;
N-(2-Dimethylamino-ethyl)-N'-[5-(3-ethoxy-benzenesulfonyl)-thiazol-2-yl]-2-trifluoromethyl-pyrimidine-4,6-diamine;
[5-(3-Ethoxy-benzenesulfonyl)-thiazol-2-yl]-[2-methyl-6-(2-pyrrolidin-1-yl-ethoxy)-pyrimidin-4-yl]-amine;
N-[5-(3-ethoxy-benzenesulfonyl)-thiazol-2-yl]-[2-methyl-((6R)-1-pyrrolidin-2-yl-methoxy)pyrimidin-4-yl]-amine;
N-[5-(3-ethoxy-benzenesulfonyl)-thiazol-2-yl]-[2-methyl-6-(pyrrolidin-3-yl oxy)pyrimidin-4-yl]-amine;
N-[5-(3-ethoxy-benzenesulfonyl)-thiazol-2-yl]-[6-(2-methoxy-ethoxy)-2-methyl-pyrimidin-4-yl]-amine;
[5-(3-Ethoxy-benzenesulfonyl)-thiazol-2-yl]-[5-fluoro-2-methyl-6-(2-pyrrolidin-1-yl-ethoxy)-pyrimidin-4-yl]-amine;
N-[5-(3-ethoxy-benzenesulfonyl)-thiazol-2-yl]-[5-fluoro-6-(2-methoxy-ethoxy)-2-methyl-pyrimidin-4-yl]-amine;
[6-(2-Cyclopentyl-ethoxy)-5-fluoro-2-methyl-pyrimidin-4-yl]-[5-(3-ethoxy-benzenesulfonyl)-thiazol-2-yl]-amine;
[6-(2-Dimethylamino-ethoxy)-5-fluoro-2-methyl-pyrimidin-4-yl]-[5-(3-ethoxy-benzenesulfonyl)-thiazol-2-yl]-amine;
[6-(2-Dimethylamino-ethoxy)-2-trifluormethyl-pyrimidin-4-yl]-[5-(3-Ethoxy-benzenesulfonyl)-thiazol-2-yl]-amine;
[5-(3-Ethoxy-benzenesulfonyl)-thiazol-2-yl]-[6-(3-methoxy-prop-1-ynyl)-2-methyl-pyrimidin-4-yl]-amine;
(3-{6-[5-(3-Ethoxy-benzenesulfonyl)-thiazol-2ylamino]-2-methyl-pyrimidin-4-yl}-prop-2-ynyl)-methyl-carbamic acid tert-butyl ester;
(3-{6-[5-(3-Ethoxy-benzenesulfonyl)-thiazol-2ylamino]-2-methyl-pyrimidin-4-yl}-1,1-dimethyl-prop-2-ynyl)-methyl-carbamic acid tert-butyl ester;
[5-(3-Ethoxy-benzenesulfonyl)-thiazol-2-yl]-[6-(3-methoxy-propyl)-2-methyl-pyrimidin-4-yl]-amine;
(3-{6-[5-(3-Ethoxy-benzenesulfonyl)-thiazol-2ylamino]-2-methyl-pyrimidin-4-yl}-propyl)-methyl-carbamic acid tert-butyl ester;
(3-{6-[5-(3-Ethoxy-benzenesulfonyl)-thiazol-2ylamino]-2-methyl-pyrimidin-4-yl}-1,1-dimethyl-propyl)-carbamic acid tert-butyl ester;
[5-(3-Ethoxy-benzenesulfonyl)-thiazol-2-yl]-[6-(3-methylamino)propyl)-2-methyl-pyrimidin-4-yl]-amine; and
[6-(3-Amino-3-methyl-butyl)-2-methyl-pyrimidin-4-yl]-[5-(3-ethoxy-benzenesulfonyl)-thiazol-2yl]-amine.

22. The compound of claim 1 having the formula:

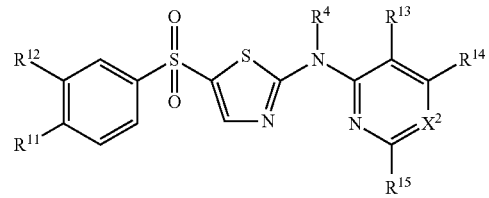

wherein $R^{11}$ is hydrogen, methoxy, trifluoromethoxy, fluoro or chloro;
$R^{12}$ is hydrogen, methoxy or ethoxy;
$R^{15}$ is hydrogen, methyl or trifluoromethyl;
$R^{13}$ and $R^{14}$ are independently hydrogen, halogen, —$CF_3$, -$L^3$-$R^7$, -$L^3$-$OR^7$, -$L^3$-$NR^8R^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
wherein $L^3$ is a bond or substituted or unsubstituted alkylene; and
$R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
wherein an $R^8$ and an $R^9$ are optionally joined with the nitrogen to which they are attached to form a substituted or unsubstituted heterocycloalkyl, or substituted or unsubstituted heteroaryl;
two $R^7$ substituents are optionally joined with the oxygen to which they are attached to form a substituted or unsubstituted heterocycloalkyl and
an $R^7$ and an $R^8$ are optionally joined with the nitrogen and oxygen to which they are attached, respectively, to form a substituted or unsubstituted heterocycloalkyl, or substituted or unsubstituted heteroaryl.

23. The compound of claim 22 wherein $R^{11}$ is H and $R^{12}$ is ethoxy.

24. The compound of claim 22 wherein $R^4$ is H.

* * * * *